United States Patent
Decoppi et al.

(10) Patent No.: US 10,632,229 B2
(45) Date of Patent: Apr. 28, 2020

(54) TISSUE ENGINEERING

(71) Applicant: UCL BUSINESS LTD, London Greater London (GB)

(72) Inventors: Paolo Decoppi, London Greater London (GB); Luca Urbani, London Greater London (GB); Anna Urciuolo, London Greater London (GB)

(73) Assignee: UCL BUSINESS LTD, London Greater London (GB)

( * ) Notice: Subject to any disclaimer, the term of this patent is extended or adjusted under 35 U.S.C. 154(b) by 2 days.

(21) Appl. No.: 15/757,729

(22) PCT Filed: Sep. 7, 2016

(86) PCT No.: PCT/EP2016/071114
§ 371 (c)(1),
(2) Date: Mar. 6, 2018

(87) PCT Pub. No.: WO2017/042232
PCT Pub. Date: Mar. 16, 2017

(65) Prior Publication Data
US 2019/0038807 A1 Feb. 7, 2019

(30) Foreign Application Priority Data

Sep. 7, 2015 (GB) .................................. 1515820.7

(51) Int. Cl.
*A61L 27/38* (2006.01)

(52) U.S. Cl.
CPC ....... *A61L 27/3886* (2013.01); *A61L 27/3804* (2013.01); *A61L 27/3834* (2013.01); *A61L 27/3882* (2013.01); *A61L 2430/22* (2013.01)

(58) Field of Classification Search
None
See application file for complete search history.

(56) References Cited

U.S. PATENT DOCUMENTS

2010/0068190 A1* 3/2010 Dimmeler .......... A61K 38/1833
424/93.7

FOREIGN PATENT DOCUMENTS

| WO | 2003/092471 A2 | 11/2003 |
| WO | 2003/095631 A1 | 11/2003 |

OTHER PUBLICATIONS

Fishman, Jonathan M; et al; "Airway tissue engineering" Expert Opinion on Biological Therapy, 11, 1623-1635, 2011 (Year: 2011).*

(Continued)

*Primary Examiner* — David W Berke-Schlessel
(74) *Attorney, Agent, or Firm* — Nixon Peabody LLP; Mark J. FitzGerald; Nicole D. Kling

(57) ABSTRACT

The present invention relates generally to methods and materials for use in the production of implants, particularly luminal tissue implants, where the implants are engineered by seeding of an acellular scaffold or matrix with muscle cell precursors and fibroblasts, for example injection seeding using particular ratios of cells. The present invention provides methods for producing tissue engineered constructs for implantation into a subject which can utilise novel seeding processes described herein for improved cell engraftment and differentiation. In addition, the invention describes methods for treating an individual by implantation of the engineered constructs or tissues of the invention.

36 Claims, 22 Drawing Sheets

(56) References Cited

OTHER PUBLICATIONS

Figure 1:
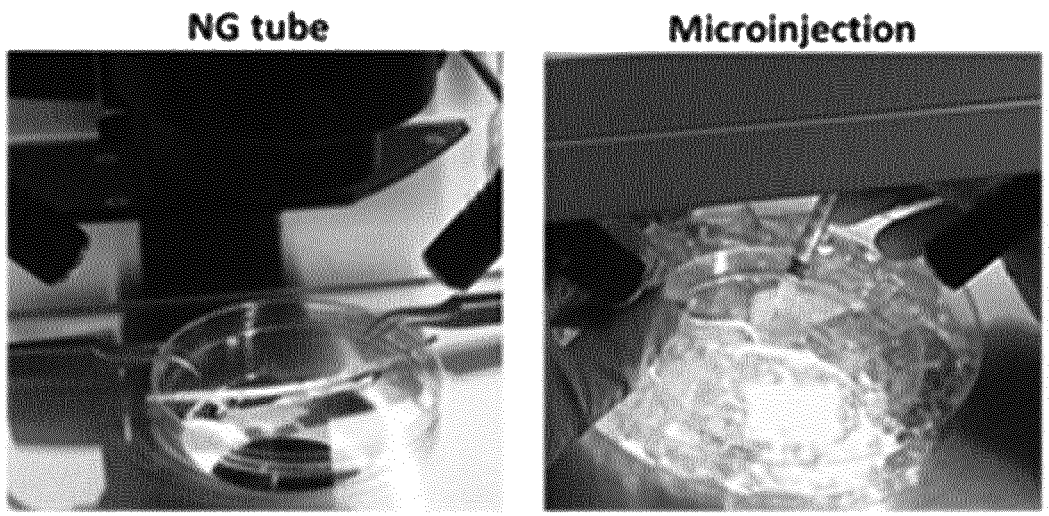

Totonelli, Giorgia; et al; "Esophageal tissue engineering: A new approach for esophageal replacement" World of Gastroenterology, 18, 6900-6907, 2012 (Year: 2012).*
Maghsoudlou, Panagiotis; et al; "Tissue engineering of the esophagus" Seminars in Pediatric Surgery, 23, 127-134, 2014 (Year: 2014).*
Carfi-Pavia et al., "Porous poly (L-lactic acid) scaffolds are optimal substrates for internal colonization by A6 mesoangioblasts and immunocytochemical analyses." Journal of Biosciences 34(6):873-879 (2009).

* cited by examiner

TISSUE ENGINEERING

CROSS-REFERENCE TO RELATED APPLICATIONS

This application is a 35 U.S.C. § 371 National Phase Entry Application of International Application No. PCT/EP2016/071114 filed Sep. 7, 2016, which designates the U.S. and claims priority under 35 U.S.C. § 119(a) to Provisional Patent Application Ser. No. GB 1515820.7 filed Sep. 7, 2015, the contents of which are incorporated herein by reference in their entireties.

TECHNICAL FIELD

The present invention relates generally to methods and materials for use in the production of implants, particularly luminal tissue implants, where the implants are engineered by seeding of an acellular scaffold or matrix with muscle cell precursors and fibroblasts. The present invention provides methods for producing tissue engineered constructs for implantation into a subject which can utilise novel seeding processes described herein for improved cell engraftment and differentiation. In addition, the invention describes methods for treating an individual by implantation of the engineered constructs or tissues of the invention.

BACKGROUND ART

Tissue or organ damage, dysfunction, or loss is a feature of a wide variety of medical conditions. In some such conditions replacement of the damaged tissue or organ is the best or even the only option.

For example, oesophageal atresia is a congenital medical condition which affects the alimentary tract and which occurs in approximately 1 in 2500 live births. It causes the oesophagus to end in a blind-ended pouch rather than connecting normally to the stomach. The most severe case of oesophageal atresia is sometimes referred to as oesophageal agenesis, where no oesophagus is present at all. The most immediate and effective treatment in the majority of cases is a surgical repair to reconnect the two ends of the oesophagus to each other.

Transplantation from human donors (either live or cadaveric) has enjoyed significant success, and procedures such as liver, heart, and kidney transplants are becomingly increasingly common. However, the severe shortage of donors, the complexity of harvesting organs and delivering them to the recipient, and the potential for transmission of infectious agents are significant shortcomings of this approach, as are its applicability to pediatric patients.

As explained in, for example, WO0214480, tissue engineering is an evolving field that seeks to develop techniques for culturing replacement tissues and organs in the laboratory.

The general strategy for producing replacement tissues utilizes mammalian cells that are seeded onto an appropriate substrate for cell culture. The cells can be obtained from the intended recipient (e.g., from a biopsy), in which case they are often expanded in culture before being used to seed the substrate. Cells can also be obtained from other sources (e.g., established cell lines). After seeding, cell growth is generally continued in the laboratory and/or in the patient following implantation of the engineered tissue.

Thus, for example, developing a construct for regeneration or substitution of damaged luminal organs (such as the oesophagus) needs a combination of scaffold and cells to produce a functional three dimensional tissue.

WO0214480 (the disclosure of which is incorporated herein by reference) describes methods for producing a tissue engineered construct by growing cells in vitro on a substrate and then decellularizing the construct to produce a decellularized construct consisting largely of extracellular matrix components. It is reported that the construct can be used immediately or stored until needed. The decellularized construct can be used for further tissue engineering, which may include seeding the construct with cells obtained from the intended recipient of the construct. During any of the growth phases required for production of the construct, the developing construct may be subjected to various tissue engineering steps such as application of mechanical stimuli including pulsatile forces. The methods also include producing an engineered native tissue by harvesting tissue from an animal or human, performing one or more tissue engineering steps on the tissue, and subjecting the tissue to decellularization. The decellularized, engineered native tissue may then be subjected to further tissue engineering steps WO2003092471 (also published as US2005/0202058) describes tissue graft constructs that include an extracellular matrix material in combination with added endothelial cells and at least one additional added exogenous cellular population.

US2014/0341862 relates to a method for preparing a tissue construct for medical purposes which uses endothelial progenitor cells (EPC) which have not been passaged multiple times and have a content of EOEC (early outgrowth endothelial progenitor cells) and LOEC (late outgrowth endothelial progenitor cells). These cells and fibroblasts and/or muscle cells, viz. myoblasts, myofibroblasts, smooth muscle cells or the progenitors thereof, are, in the form of living cells, seeded onto a matrix or introduced into a matrix in order to yield the tissue construct following further treatment steps. The matrix is preferably a protein preparation, more particularly a fibrinogen preparation.

US 2004/0028662 relates to a cell colonisation process whereby biological cells are colonised on an synthetic or natural tissue matrix in order to obtain a tissue implant or tissue transplant. The growth of the cells is promoted by the addition of mediators, factors or co-factors supplied by co-cultivated cells.

WO03/095631 relates to multipotent stem cells, methods for their isolation and in vitro expansion, processes for their in vitro differentiation, and their use for regenerating or repairing biological tissues.

Unfortunately, existing approaches for cell seeding techniques and cell combinations in tissue engineering often show low cell engraftment and lack of a homogeneous population of cells on the scaffold. This inhibits the development of a functional tissue, particularly luminal tissue or organs.

Thus it can be seen that novel methods for seeding scaffolds of matrices for producing implantable luminal tissue or organs with improved cell engraftment or related properties would provide a contribution to the art.

DISCLOSURE OF THE INVENTION

Surprisingly, the inventors have demonstrated that seeding a combination of muscle cell precursors and fibroblasts into a tissue scaffold or matrix to engineer a construct for repair or replacement of an organ, in accordance with the methods of the invention, can improve cell engraftment and colonization of the 3D matrix.

In preferred embodiments, a combination of fibroblasts and muscle cell precursors is injected into the wall of a scaffold for oesophageal tissue engineering. Injection provides successful distribution of the cell suspension directly inside the scaffold.

Without wishing to be bound by theory, it is believed that the delivery of the two above described cell populations allows the establishment of a paracrine effect between the two cell lines. This unexpectedly results in improved cell engraftment, proliferation, and migration/invasion across the scaffold, as well as differentiation of the muscle cell progenitors towards mature muscle cells. Furthermore the presence of muscle cells and fibroblasts mimics the heterogeneity of a vital tissue and the presence of the two cell types can obviate the need for adding multiple exogenous growth factors or adhesion molecules to the culture.

Further, the inventors have surprisingly found that using an equal or higher ratio of muscle cell precursors to fibroblasts provides a homogenous distribution of cells, while reducing the possibility of overgrowth of the fibroblasts. The resulting product thus more closely reflects the naturally occurring tissue and thus is desirable.

Thus, delivery of the cell types in accordance with the preferred protocols described herein has been shown to provide a more homogenous distribution of cells through the different layers of the tissue, and thereby provide a construct which is more similar to native tissue.

The present invention provides methods for producing tissue engineered constructs for implantation into the body which utilise novel seeding processes described herein for improved cell engraftment and differentiation. In addition, the invention describes methods for treating an individual in need of replacement or enhancement (e.g. repair) of a tissue or organ by implantation of the engineered constructs or tissues of the invention. These and other aspects of the invention will now be described in more detail.

In one aspect the present invention provides a method of producing or engineering a tissue or organ construct, for example a luminal or other hollow tissue construct, the method comprising the steps of:
(i) providing a scaffold or matrix
(ii) seeding a combination of mesoangioblasts and fibroblasts into and/or onto the matrix, wherein said mesoangioblasts and fibroblasts are seeded separately, simultaneously or sequentially; and
(iii) culturing the seeded scaffold to produce an implantable construct.

In accordance with the invention, the tissue or organ construct comprises mammalian tissue produced by proliferation and/or differentiation of the seeded mesoangioblasts and/or fibroblasts, preferably by proliferation of both cell types and by differentiation of the mesoangioblasts on and/or in the scaffold provided. The production method of the invention and thus the generation of the luminal tissue or organ construct is generally carried out in vitro.

It will be appreciated however that further cell proliferation and/or differentiation and generation of the construct can occur after implantation in vivo. Thus, preferably the production of the construct is carried out in vitro until a construct is generated which is sufficiently populated with cells and/or where precursor cells (mesoangioblasts) are sufficiently differentiated to allow successful implantation into a subject.

Further cellular proliferation in and/or on the scaffold can then subsequently occur e.g. after implantation. It will be appreciated therefore that a scaffold need not be entirely populated with the seeded cells to be useful for implantation into a subject (e.g. it is possible that the scaffold has areas where seeded cells are not present, for example the scaffold may have seeded cells across at least 70, 80, 90, 95 or 99% of its surface).

The size and/or shape of the tissue or organ construct generated may be typically representative of the size/shape of the injury and/or damage which is to be treated in a subject or patient in need of said tissue or organ construct.

Thus, for example, if a subject is lacking a portion of a luminal tissue/organ, the tissue or organ construct produced may correspond to the size/shape of the missing portion. Alternatively, the tissue or organ construct generated may be of a larger size than the size of the injury/damage in the luminal organ in a subject e.g. at least 5, 10, 15, 20, 30, 40 or 50% larger and such a larger construct may be implanted or the construct may be appropriately sized/shaped after production. The size and dimension of the construct may further depend on the age and size of the subject recipient for the implantation.

Reference to a "luminal" construct, or the like, refers to a construct which is suitable for replacement of, or implantation into, a luminal organ or tissue, such as those described below, rather than strictly the structure of the construct itself. Reference to tissue constructs should be understood accordingly. Thus reference to an oesophageal construct refers to a construct which is suitable for implantation into the oesophagus, or as an oesophageal replacement, and a bowel construct refers to a construct which is suitable for implantation into the bowel, or as a bowel replacement.

In one embodiment, the construct may have a luminal or tubular shape, if for example said construct is to be used to provide a missing or absent portion of the luminal organ, or replace it entirely. However, a luminal construct does not necessarily have a luminal or tubular shape, and as discussed above the shape is entirely dependent on the tissue to be replaced, inserted or repaired.

As described previously, the produced or generated tissue or organ construct will comprise the scaffold or matrix (particularly an acellular matrix or scaffold, such as a decellularized scaffold or a polymeric scaffold) and a homogenous distribution of cells (differentiated mesoangioblasts/non-differentiated mesoangioblasts and fibroblasts). Optionally this can be further modified or combined with other means for connection or mounting in the recipient's body.

Further, the tissue or organ construct may comprise other cell types, particularly epithelial and\or endothelial or neural crest cells. In a further embodiment, the method of the invention comprises an additional step of seeding epithelial cells onto the construct or in and/or onto the scaffold prior to implantation.

The terms "tissue" or "organ" are used interchangeably herein with respect to the construct, unless context demands otherwise.

The protocols for producing strong, resilient smooth muscle containing constructs described herein may be applied to luminal\hollow (the terms are used interchangeably unless context demands otherwise) organs such as oesophagus, trachea, blood vessels, intestine, urethra, bowel etc. The tissue or organ construct produced by a method of the invention has particular utility as an oesophageal construct. Further, the tissue or organ construct produced in accordance with the above method has particular utility as a bowel construct. The constructs produced by the methods of the invention (e.g. oesophageal and bowel constructs) are particularly suitable for the treatment of a neonate or infant.

As described above, the inventors have surprisingly found that introduction of an equal or higher ratio of mesoangioblasts:fibroblasts results in an advantageous homogenous distribution of cells in the tissue construct. Hence, in a preferred embodiment a combination of mesoangioblasts:fibroblasts within the following ranges of proportions 50:50 to 99:1; 65:35 to 90:10; 70:30 to 90:10; 80:20 to 90:10; 83:17 to 88:12 for introduction to the scaffold or matrix is encompassed. Preferably, a ratio of mesoangioblasts:fibroblasts equal to or greater than 70:30 may be used, with a particularly preferred ratio of about 85:15.

It will be understood that a "combination" of mesoangioblasts and fibroblasts may be seeded simultaneously, sequentially or separately. Thus, the cells do not need to be introduced together and/or at the same time, and "combination" in this context should not be taken to imply simultaneous delivery of the cells. Sequential delivery may involve delivering the cell populations within at least 1, 2, 5, 10, 20, 30, 40, 50, or 60 minutes of each other, or within or about 1, 2, 3, 4, 5, 6, 7, 8, 9, 10, 11, 12, 24, 36 or 48 hours of each other. However simultaneous delivery is preferred, wherein the cells are introduced together from either separate sources or from the same source, where the cells are preferably pre-mixed together in a suitable ratio as described above.

For seeding purposes the cells may be delivered in a suitable medium such as those well known in the art. Examples include MEGACELL, DMEM, etc., or gels such as Matrigel etc. The medium may contain collagen, fibronectin, or the like.

The cell density to be applied may typically be in the range of $1\times10^8$ to $1\times10^{10}$ cells/mL, for example about $1\times10^9$ cells/mL.

Preferably the seeding is carried out by injection into the scaffold or matrix, preferably into the muscle layer of the matrix. Suitable sources of matrix are discussed in more detail hereinafter. The inventors have determined that injection in this way provides a superior product compared to superficial application of cells.

In a particularly preferred embodiment, the cells may be seeded onto and/or into the scaffold or matrix by co-injection.

The volume of medium to be applied will depend on the cell density, but a preferred injection this will typically be in the range 1 to 50 µL, for example 1 to 50 µL, most desirably 5-10 µL e.g. about 5 µL.

Optimally the flow rate whilst delivering injectate is in the range of 1 to 25 µL/s, for example 1 to 10 µL/s e.g. about 5 µL/s.

Multiple seedings of cells may be carried out on the scaffold. Thus, preferably the seeding is achieved by multiple injections to ensure that the cells are dispersed across the scaffold as much as possible. It is desirable that the density of cells be at least $10^5$, $10^6$ or $10^7$ cells/5 mm length, more preferably a density of about $10^6$ cells/5 mm length, which has been shown to lead to highly effective engraftment. Thus, for example, at least one application (e.g. injection of cells is carried out, particularly at least 2, 3, 4, or 5 applications (e.g. injections). It will be appreciated that the numbers of injections may be dependent on the size and shape of the scaffold.

By way of non-limiting example, a typical oesophageal construct suitable for a neonate may be around 8-10 mm across and 4-5 cm long when in the relaxed state, Such a construct may be subjected, for example, to 3 injections every 5 mm ring (circumferentially)

Tubular scaffolds may be cannulated e.g. with an NG tube to allow easier access and handling for seeding "Mesoangioblasts" as used herein refers to precursor or progenitor muscle cells, and are precursor cells for the smooth muscle layer present in large vessels.

Mesoangioblasts typically express markers such as alkaline phosphatase (AP) and NG2.

The term "precursor cell" refers to a cell that is not fully differentiated but that has the capacity to either become more fully differentiated itself or to give rise to a cell (or cells) that is able to further differentiate. The precursor cell may give rise to one or more different cell types. The process by which the precursor cell gives rise to a cell (or cells) that is able to further differentiate may involve one or more rounds of cell division. The term "progenitor cell" also includes cells that may have undertaken one or more steps along a differentiation pathway, e.g., that express one or more differentiation markers, for example the smooth muscle differentiation markers SM22 and aSMA.

The term "fibroblasts" is to be understood in the most general sense, including fibroblasts circulating in the blood.

The cells used in the present methods will typically be autologous i.e. originate from or are derived from the intended recipient of the tissue or organ construct generated by the method of the invention. However, cells for use in the method may also be allogeneic, i.e. obtained or derived from a subject who is not the recipient of the tissue or organ construct to be generated. Further, xenogeneic cells may be used, i.e. cells derived from a different species to the recipient of the tissue/organ construct.

Cells for use in the present method may be obtained via a small biopsy (e.g. from muscle) from the patient and the cells isolated e.g. using GMP-grade collagenase and neutral protease.

Particularly, mesoangioblasts and fibroblasts to be used in the method may conveniently be obtained from the same biopsy. Other cells may also be used in the method of the invention and/or may be present in the produced tissue or organ construct. Particularly, epithelial cells may be present, which may be obtained from the same or different biopsy to the mesoangioblast/fibroblast cells. Further, smooth muscle cells may be present.

In one example protocol, small (2-3 mm) muscle biopsies may be plated on Matrigel/Collagen gel in selective Medium (Megacell) to promote cell outgrowth. Cells may be grown in Megacell medium and passaged when 60-70% confluent.

Further, the method may be performed in the absence of endothelial progenitor cells and thus the produced tissue or organ construct may not comprise endothelial cells in one embodiment.

Once the cells have been passaged they can be utilised for seeding. For example they may be trypsinised (e.g. between passage 3, 4, 5, 6 or 7) and then suspended in the selected gel or medium and kept on ice.

The methods of the present invention require a scaffold or matrix (the terms are used interchangeably herein) for seeding.

Particularly, an acellular scaffold or matrix is used, for example, a decellularized scaffold or a polymeric scaffold. Such scaffolds and methods for their production are well known in the art. For example WO0214480 refers to five general categories of scaffold in the art: (1) non-degradable synthetic polymers; (2) degradable synthetic polymers; (3) non-human collagen gels, which are non-porous; (4) non-human collagen meshes, which are processed to a desired porosity; and (5) human (cadaveric) decellularized collagenous tissue.

An "acellular" scaffold typically does not comprise cells or cellular components. However, it will be appreciated that for example where a scaffold is used from a biological source, e.g. a decellularised scaffold, it is possible that some cells may remain on the scaffold e.g. after decellularisation, as discussed below.

In one embodiment herein the scaffold is an artificial a synthetic polymer scaffold. Examples of synthetic polymers include Dacron and Teflon which may be processed into a variety of fibres and weaves. Other polymers used as synthetic tissue matrices include polygalactide and polydioxanone.

Other synthetic scaffolds may be proteinaceous in nature e.g. primarily consist of purified proteins such as collagen.

Non-synthetic scaffolds may also be proteinaceous in nature, or primarily consist of a collagenous extracellular matrix (ECM).

Preferably the scaffold will be a decellularized (biological) matrix, for example derived from a luminal organ such as the oesophagus. Typically, the scaffold is derived from the luminal organ or tissue type into which the produced tissue or organ construct is required for implantation. For example, if the tissue or organ construct is required for implantation into the oesophagus, then typically the scaffold may be produced from a decellularized oesophagus, e.g. from another source.

In one embodiment neonatal human donor tissue may be used. In another the scaffold may be derived from human cadaver.

Preferably, for practicability, the scaffold may be xenogeneic i.e. it originates from or is derived from a donor of a different species than the recipient, for example, a human recipient.

In this connection, substrates suitable for decellularization are, inter alia, decellularized animal-derived scaffolds e.g. porcine-derived, rat derived or rabbit derived. For example in a preferred embodiment the scaffold may be a decellularized piglet oesophagus.

Any known decellularization method can be employed to provide the scaffold. In general decellularization methods employ a variety of chemical, biochemical, and/or physical means to disrupt, degrade, and/or destroy cellular components and/or modify the matrix in which the cells are embedded so as to facilitate removal of the cells and cellular components, typically leaving an ECM scaffold. WO0214480 (supra) describes methods of decellularizing native tissues. The invention encompasses the use of decellularized scaffolds produced by any decellularization technique that removes a substantial fraction of the cells while leaving the matrix substantially intact.

Removal of a "substantial fraction" of the cells refers to the removal of at least 60, 70, 80, 90, 95 or 99% of the cells. Reference to leaving the matrix "substantially intact" refers to retaining the presence of at least 40, 50, 60, 70, 80, 90, 95 or 99% of the matrix e.g. of the ECM.

The invention further provides a method as described above additionally including a step of obtaining a scaffold or matrix by decellularization of an appropriate substrate (e.g. those as set out above, particularly a porcine-derived substrate).

The scaffold may typically be any shape or size, particularly it may correspond to the size/shape of the tissue which is required to be replaced, repaired or treated in a subject. Alternatively, the scaffold may be larger or even smaller than the injury (cell proliferation can occur in vivo).

Following seeding of the cells, in certain embodiments of the invention, the populations of cells are allowed to adhere to the matrix for a period of time prior to placing the seeded scaffold in culture medium. It will be appreciated that it may not be necessary for all seeded cells to adhere to the matrix. Particularly however, at least 60, 70, 80 or 90% of the seeded cells may adhere.

Furthermore, as explained in WO0214480, various treatments may be applied to enhance adherence of cells to the scaffold. Appropriate treatments are described, for example, in U.S. Pat. No. 5,613,982. Such treatments include the application of various proteins, e.g., growth factors or extracellular matrix proteins to the scaffold or to the growing construct. For example, collagen, elastin, fibronectin, laminin, or proteoglycans may be applied to the substrate. The substrate can be impregnated with growth factors or these agents may be provided in the culture medium.

In the methods of the invention, the cell-seeded construct is cultured for a growth period in an environment suitable for growth of the cells to form an engineered construct.

Appropriate growth conditions for mammalian cells in culture are well known in the art. Cell culture media generally include essential nutrients and, optionally, additional elements such as growth factors, salts, minerals, vitamins, etc. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art.

Preferably cells are cultured under sterile conditions in an atmosphere of about 5% $CO_2$ at a temperature at or near the body temperature of the animal of origin of the cell. For example, human cells are preferably cultured at approximately 37° C.

In general, the length of the growth period will depend on the particular tissue engineered construct being produced. The growth period can be continued until the construct has attained desired properties, e.g., until the construct has reached a particular thickness, size, strength, composition of proteinaceous components, cell density, or expression of appropriate cell markers—for example Mesoangioblast-derived smooth muscle cells should express markers such as SM22, alphaSMA, Calponin. Methods for assessing these parameters are described in U.S. Pat. No. 5,613,982 and the Examples hereinafter.

Typically culture of the seeded construct will be in a "bio reactor".

As discussed, for example in US2014/0341862, reactors suitable for a very wide variety of different tissue constructs are known in the prior art. Suitable for tubular constructs are, for example, a reactor as depicted in DE 199 15 610 (Bader), or one as described in EP 0 320 441 (Sulzer). The tubular vessel may be clamped in such a reactor and thus subjected to through-flow of medium or blood, as comes closest to the subsequent natural situation of integration in the body. In the Examples hereinafter, dynamic culture has been shown to be superior to static conditions, for example in respect of improved cell distribution and migration.

Through flow may be continuous flow. Through-flow may be effected in a pulsatile manner in order to imitate the influence of the heartbeat and the blood circulation. These measures can improve the mechanical strength of the construct obtained and stimulate the organization of the cells to yield a natural assembly. A preferred dynamic culture system incorporates mechanical stimulation ("peristaltic-like" culture) for improving muscle engraftment index. U.S. application Ser. No. 09/109,427 describes how a pump in communication with the interior of a body in the chamber may be used to provide cyclic increases in pressure to cause the distensible body to distend within the lumen of the construct and impart a pulsatile stretching force to the construct.

This bioreactor may incorporate a removable cassette which can be transferred from a decellularization bioreactor, subjected to seeding, and then introduced to a recellularisation bioreactor.

In use, the tubular construct may be sutured to two inserts (e.g. glass or plastic) that allow separating the inner and external compartment of the chamber. The culture chamber (connected to the bioreactor and the reservoir) may be then we filled up with proliferating medium in both compartments.

The chamber may then be incubated in a static condition before starting the flow in the inner chamber for dynamic culture.

After a period of time (for example about 24 or 48 hours) of culture, the medium can be changed from proliferation to differentiation medium both in the chamber and the reservoir—for example a preferred protocol is around 1 to 2 days in proliferation medium such as Megacell, followed by 9 days in differentiation medium (such as DMEM low serum enriched with TGFbeta). The dynamic culture can be stopped after an appropriate time which is typically between 6 and 14 days e.g. 9 days, with at least one complete medium change during that time. However culture may be longer e.g. for up to 21 or 28 days.

Optionally scaffolds can be implanted in the omentum or other ectopic site for e.g. 4-6 weeks prior to orthotopic transplantation to enhance vascularization.

Further, following culture, and prior to use, it may be desired to epithelise one or more surfaces of the scaffold, for example the surface which be the luminal surface in use. Where the scaffold or construct is itself of luminal or tubular shape, it may be desirable to epithelise the luminal side or surface of the scaffold or construct (i.e. the inside surface of the tubular or luminal shaped scaffold or construct).

The method of the invention may thus comprise an additional step of seeding epithelial cells on the construct. The construct may then be subjected to further culture if necessary.

The comments made in respect of obtaining the mesoangioblasts and fibroblasts apply mutatis mutandis to providing the epithelial cells for delivery and seeding onto the construct. For example primary cells derived from a biopsy of the subject for whom the construct is intended, and in particular from the luminal organ (which may be damaged, or vestigial) of that subject.

Following epithelial seeding, the construct will be further cultured to permit growth or expansion of the epithelial layer, prior to use.

In another aspect of the invention, there is provided a tissue or organ construct (e.g. luminal tissue or organ) obtained or obtainable according to the methods of the invention. Particularly, the tissue or organ construct is suitable for implantation and anastomosis at its intended site.

In a preferred embodiment, the invention provides an oesophageal or bowel construct obtained or obtainable by the methods of the invention. In a particular aspect, an oesophageal construct may be suitable for implantation into a neonate or infant. As discussed previously, it will be appreciated that the dimensions of the construct will be dependent on the subject receiving the construct and the organ injury or damage which has been experienced.

Further, it will be appreciated that said construct will comprise the scaffold, fibroblasts and differentiated and non-differentiated mesoangioblasts. Particularly, in the construct, it is preferred that differentiation of the introduced/seeded mesoangioblasts has occurred. Therefore in a particular embodiment, all of the seeded mesoangioblasts will have differentiated into muscle cells. However, it is possible that some of the seeded mesoangioblasts will not have differentiated or not have fully differentiated in the construct. Particularly, at least 20, 30, 40, 50, 60, 70, 80, 90, 95 or 99% of the mesoangioblasts may have differentiated to or began differentiation to muscle cells (smooth muscle cells) in the constructs. Differentiation of mesoangioblasts to muscle cells can be easily assessed by measurement of the marker SM22, or others described herein.

In a further embodiment, a luminal tissue or organ construct is provided comprising a scaffold, smooth muscle cells, fibroblasts and optionally comprising mesoangioblasts, wherein preferably said smooth muscle cells and/or mesoangioblasts are present in a ratio of 50:50 to 99:1 compared to fibroblasts, most particularly in a ratio or at least 70:30 or 85:15.

In another aspect, the invention provides methods of treating a subject in need of replacement or repair of a tissue or organ, or suffering from tissue or organ damage and/or loss, using a tissue or organ construct of the invention, preferably one incorporating autologous cells from that individual.

The term "subject" or "patient" as used herein refers to any mammal, e.g. a domestic animal such as a dog, cat etc., an agricultural animal, such as a horse, pig or cow etc., or a human. Particularly, the subject or patient may be a neonate or infant, particularly a human neonate or infant, for example who is suffering from oesophageal atresia, whereby the construct is an oesophageal construct.

Reference to replacement of a tissue or organ refers to replacement of a part or all of a luminal tissue or organ, such as those described previously. Thus, organ replacement can refer to replacement of for example at least 5, 10, 15, 20, 30, 40, 50, 60, 70, 80, 90, 95 or 100% of an organ or tissue. Replacement of an organ or tissue may be required where the organ or part thereof is missing, diseased or damaged and/or where the organ or part thereof is non-functional or has reduced function.

Tissue damage or organ damage may occur due to disease e.g. cancer or exposure to a damaging agent, such as a chemical or heat e.g. a burn. Thus, a part or all of the tissue or organ may be damaged. Further, "tissue or organ loss" may result from such damage or may for example be present at and before birth (e.g. a birth defect or congenital condition). Loss of a tissue or organ may be partial or complete loss of the organ or tissue.

As discussed previously, a construct of the invention may be used to treat a subject in need of oesophagus replacement or suffering from oesphageal damage or loss. Such a method preferably utilises a construct suitable for implantation into the oesophagus e.g. one which uses an oesophagus derived decellularized scaffold or matrix.

In a preferred embodiment, the invention provides a method of treating a subject suffering from oesophageal atresia or agenesis with a luminal tissue or organ construct of the invention (e.g. an oesophageal construct).

The term "oesophageal atresia" refers to a condition where the oesophagus ends in a blind pouch and is not connected to the stomach and "oesophageal agenesis" as used herein refers to a particularly severe case of oesophageal atresia where the oesophagus is entirely absent.

In a further preferred embodiment of the invention, a method of treating bowel damage or loss or of treating a subject in need of bowel replacement is provided, preferably, by the administration of a luminal construct of the invention (e.g. a bowel construct, produced using a decellularized bowel scaffold).

In certain embodiments, the methods comprise providing an implantable luminal tissue or organ construct of the invention (e.g. according to the methods of the invention) and implanting the construct or tissue into the body of the individual in accordance with standard surgical procedures—for example orthotopic implantation or transplantation.

After implantation, cells from the individual may migrate into the tissue in vivo, complementing the seeded cell population. The migration of cells into the construct may be enhanced, e.g., by treating the construct with growth factors, chemotactic agents, or other compounds prior to or after implantation.

Thus a method of treatment according to the invention may comprise the step of surgically implanting into a patient a construct of the invention.

Alternatively viewed, the invention provides a construct of the invention for use in the treatment of tissue or organ damage or loss or for tissue or organ replacement. Particularly, the invention provides a construct for use in the treatment of oesophageal atresia or oesophageal agenesis.

Further, the invention provides the use of a construct of the invention in the manufacture of a medicament for the treatment of tissue or organ damage or loss or for the replacement of a tissue or organ in a subject.

Also provided is use in surgery of a construct according to the invention.

Also provided is a construct according to the invention for use in surgery.

Also provided is a construct according to the invention in the manufacture of a product for use in surgery.

In another aspect there is provided a use of fibroblasts to improve cell engraftment and colonization (including improved migration and\or homogeneity) by mesoangioblasts of a 3D scaffold or matrix as described herein (e.g. tubular, for use with a luminal organ) and in particular to minimise fibrosis. Preferably the fibroblasts are used in a ratio of mesoangioblasts:fibroblasts within the following ranges of proportions 50:50 to 99:1; 65:35 to 90:10; 70:30 to 90:10; 80:20 to 90:10; 83:17 to 88:12. A preferred ratio is about 85:15.

An "improvement" of cell engraftment and colonisation may include for example, an increase in the number of seeded cells adhering to the matrix (e.g. an increase of at least 10, 20, 30 or 40%) and/or as discussed above, an improvement in migration of mesoangioblasts across the scaffold, as compared to scaffolds seeded without fibroblasts or with a sub-optimal ratio of mesoangioblasts:fibroblasts. "Improved migration" may include an increase in the rate at which mesoangioblasts populate the scaffold (e.g. a reduction in the time taken to populate the scaffold), an increase in the number of mesoangioblasts migrating across the scaffold and/or an increase in the distance over which the mesoangioblasts migrate. Any one or more of the rate of migration, the number of cells migrating or the distance migrated may increase by at least 10, 20, 30 or 40% compared to mesoangioblasts seeded on a corresponding scaffold (i.e. the same or substantially the same scaffold) in the absence of fibroblasts.

Any sub-titles herein are included for convenience only, and are not to be construed as limiting the disclosure in any way.

The invention will now be further described with reference to the following non-limiting Figures and Examples.

Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1: NG tube placement and microinjection of fMABS into the muscle wall of oesophageal matrix in sterile conditions.

Figure 2:
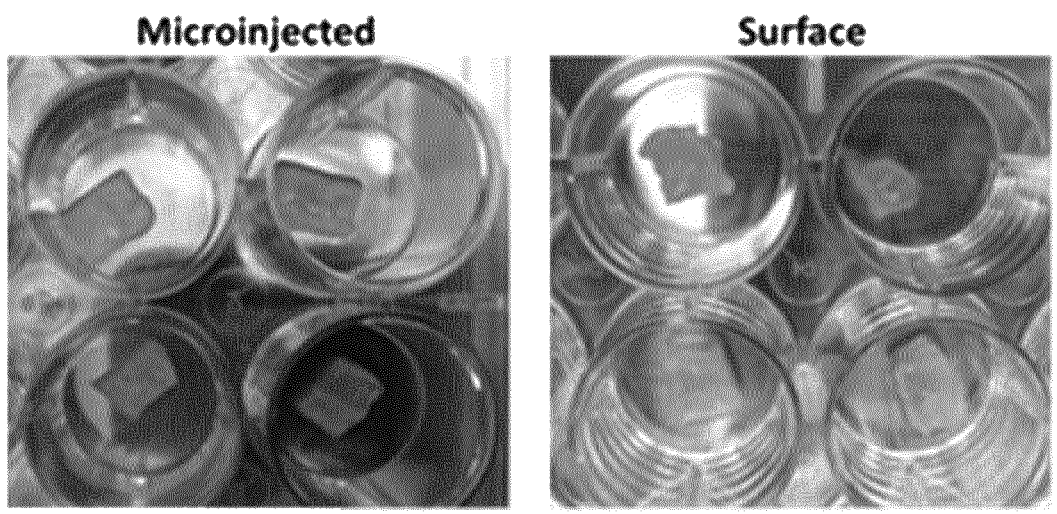

FIG. 2: Microinjected and surface seeded scaffolds, opened longitudinally and placed in 24 multiwell plates for static culture.

Figure 3:

FIG. 3: Culture chambers utilised in the culturing of constructs.

Figure 4:
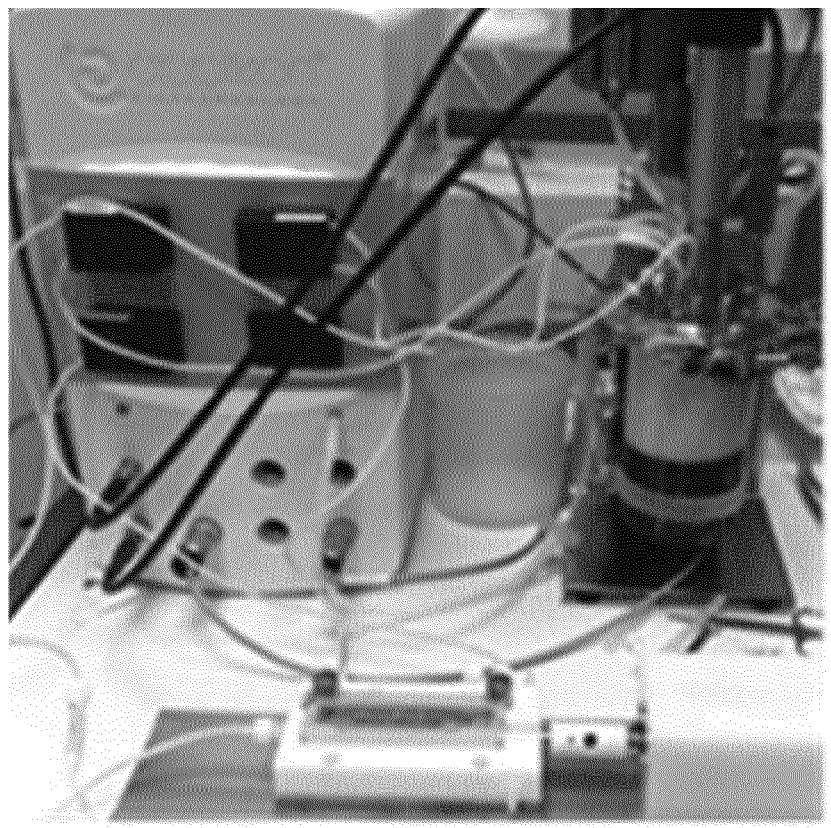

FIG. 4: Bioreactor and culture chamber.

Figure 5:
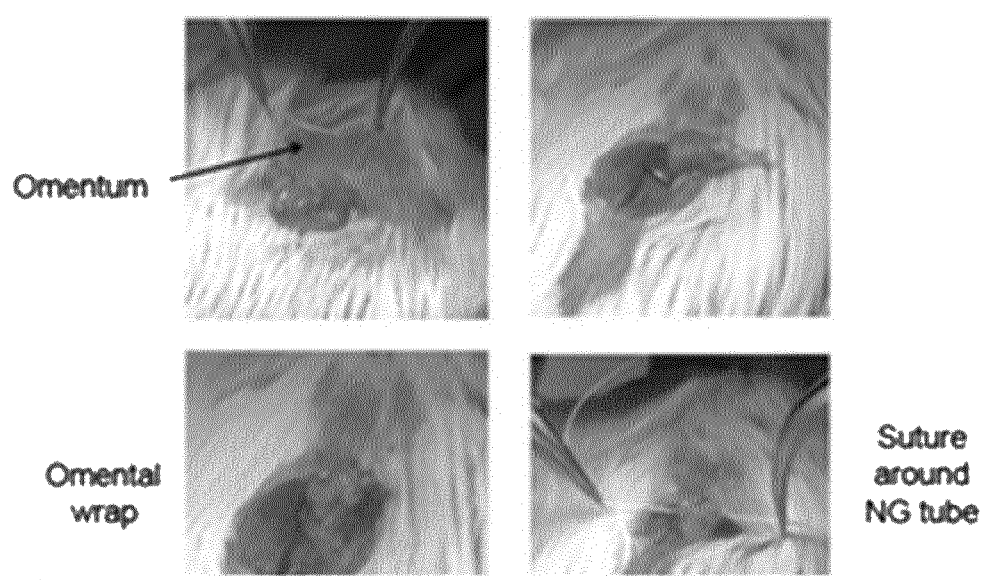

FIG. 5: Omental implantation of seeded oesophageal scaffolds into immune-compromised mice.

Figure 6:
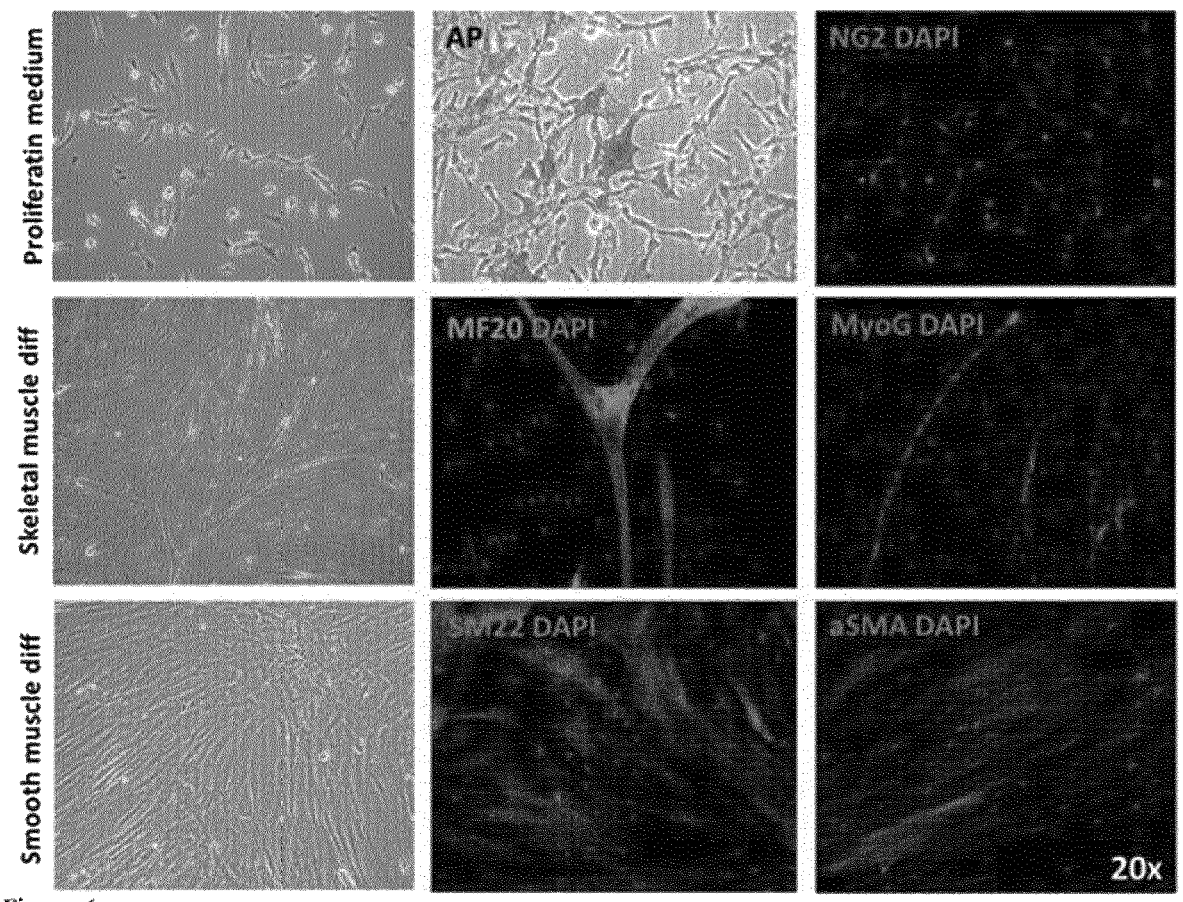

FIG. 6: fMABS cultured in proliferating medium expressed AP and NG2 markers. When cultured in skeletal muscle differentiation medium they fused forming myotubes positive for MF20 and containing MyoD positive nuclei. fMABS also showed smooth muscle differentiation markers when cultured with specific medium expressing SM22 and aSMA in culture.

Figure 7:
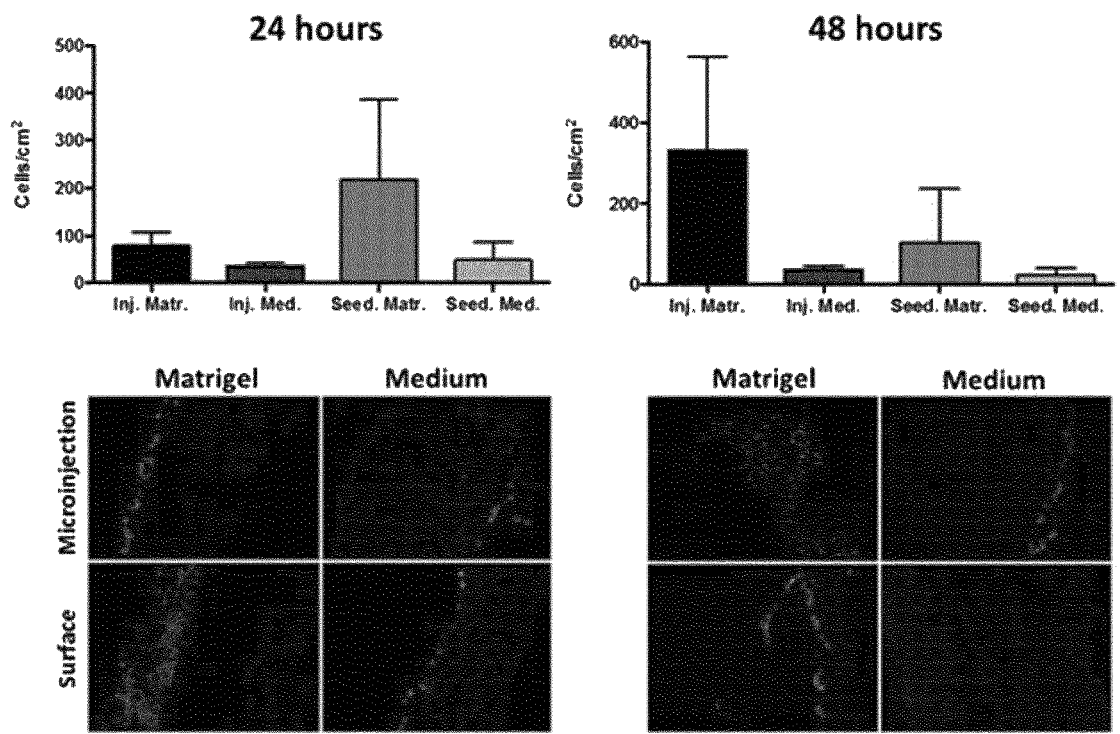

FIG. 7: Cell counting (graphs) from DAPI images of seeded rat oesophageal scaffold with cells delivered either with Matrigel or medium through microinjections or surface seeding.

Figure 8:
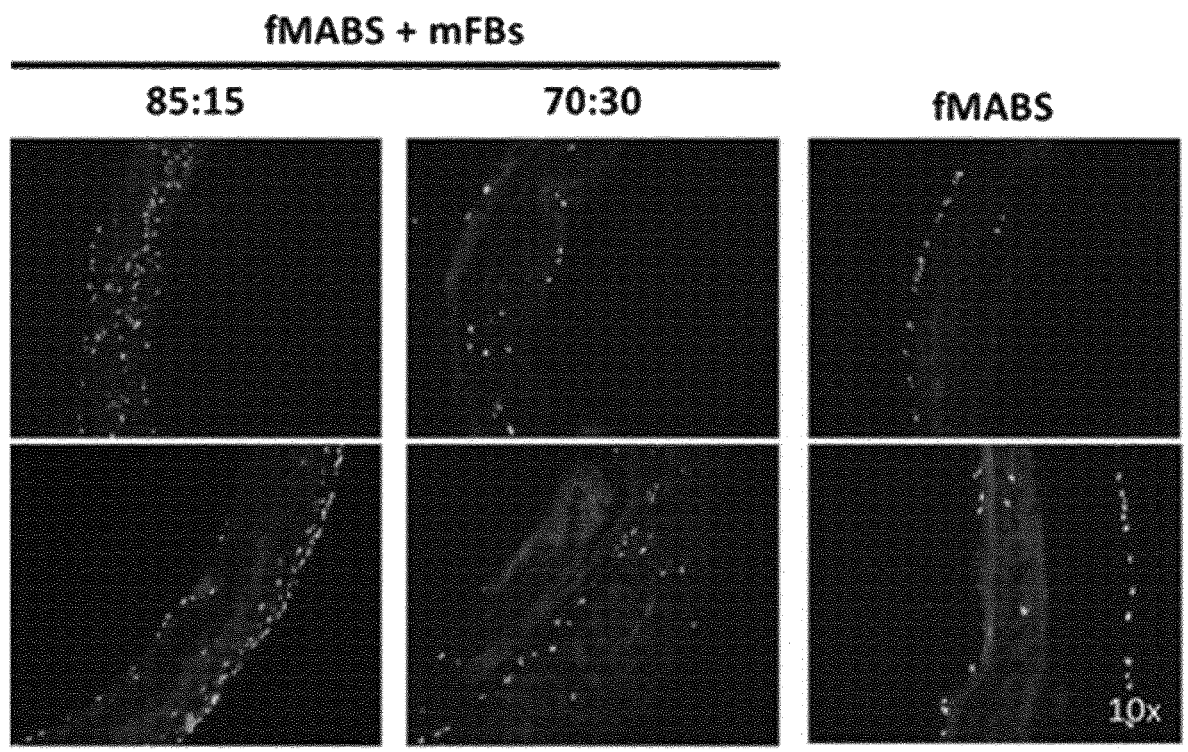

FIG. 8: Co-seeding experiment of fMABS seeded together with mouse FBs or alone. Representative pictures with DAPI staining.

Figure 9:
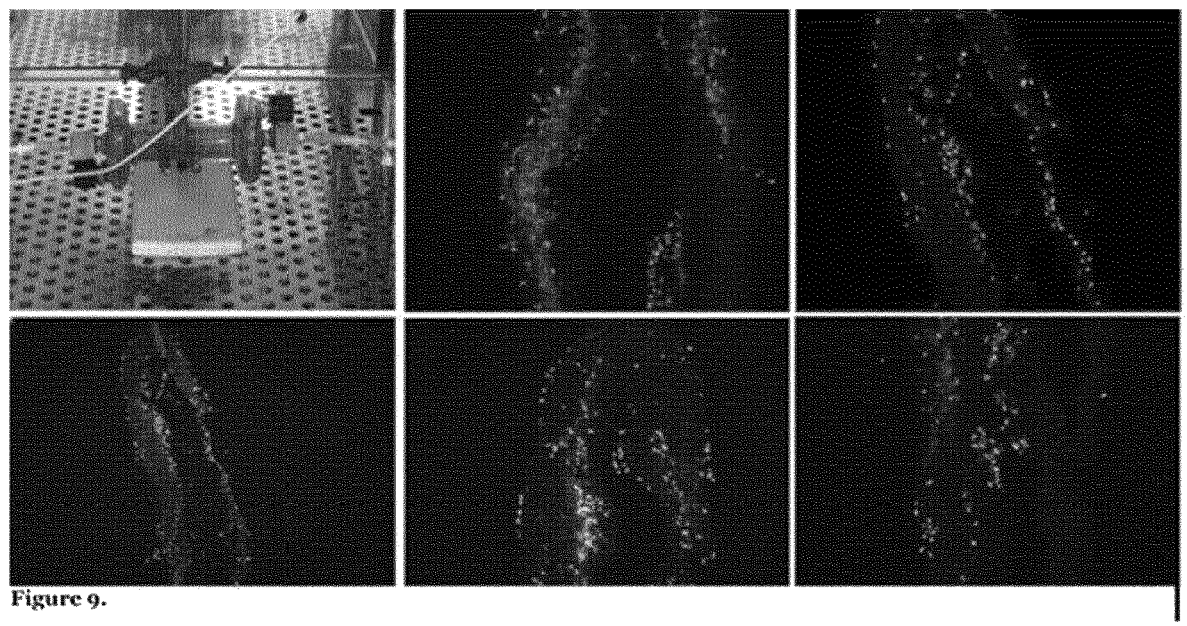

FIG. 9: Culture chamber set up in the initial static culture within the first 24 h. DAPI staining of cryosections of the dynamic cultured scaffold seeded with fMABS.

Figure 10:
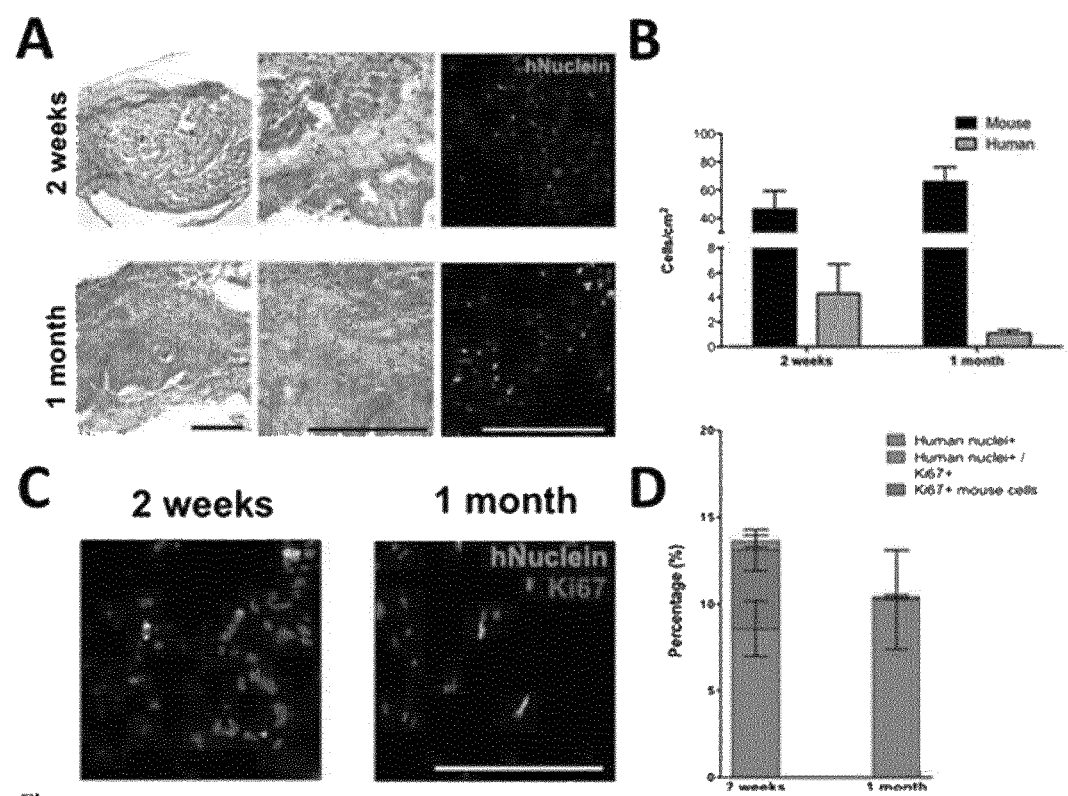

FIG. 10: (A) H&E and human nuclei immunofluorescence on sections of seeded scaffolds implanted in the omentum of nude mice for 2 and 4 weeks. (B) Cell number per area counted in random pictures of DAPI stained sections. (C) Co-staining of human nuclei and Ki67 marker. (D) Percentage of cells positive for human nuclei, double positive for human nuclei and Ki67 (mouse cells) or only Ki67 (mouse cells). These 3 categories are shown from top to bottom on the left hand bar. As explained below, after 1 month mainly human nuclei cells are present.

Figure 11:
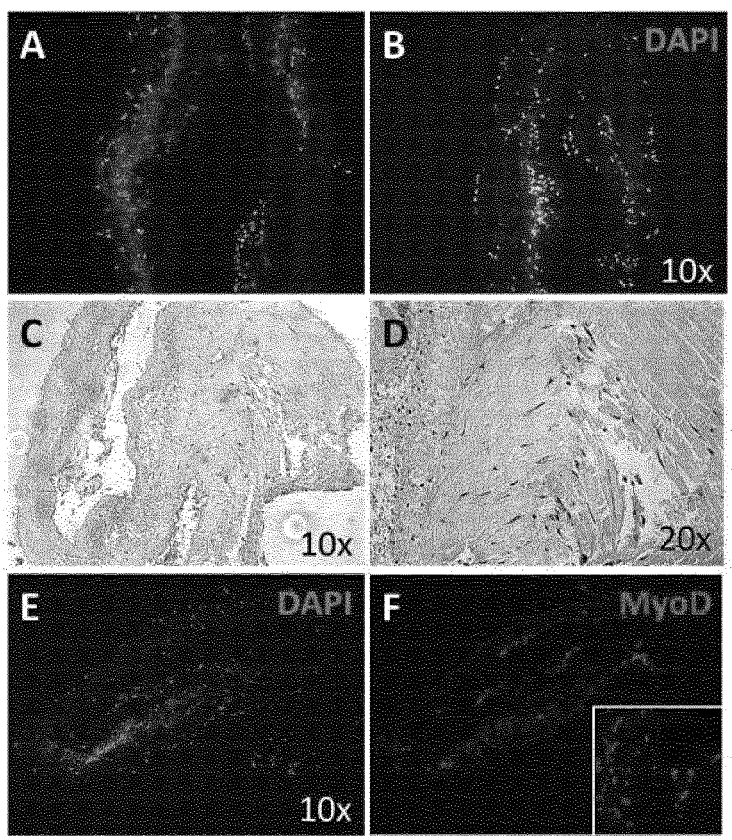

FIG. 11: DAPI staining of cryosections obtained from the cultured scaffold showing cell engraftment and proliferation inside the matrix (FIG. 11A,B), cell distribution and migration stimulated and improved by the dynamic culture condition (H&E, FIG. 11C,D). Skeletal muscle differentiation was determined with MyoD staining, a specific marker for skeletal muscle precursor cells (FIG. 11E,F)

Figure 12:
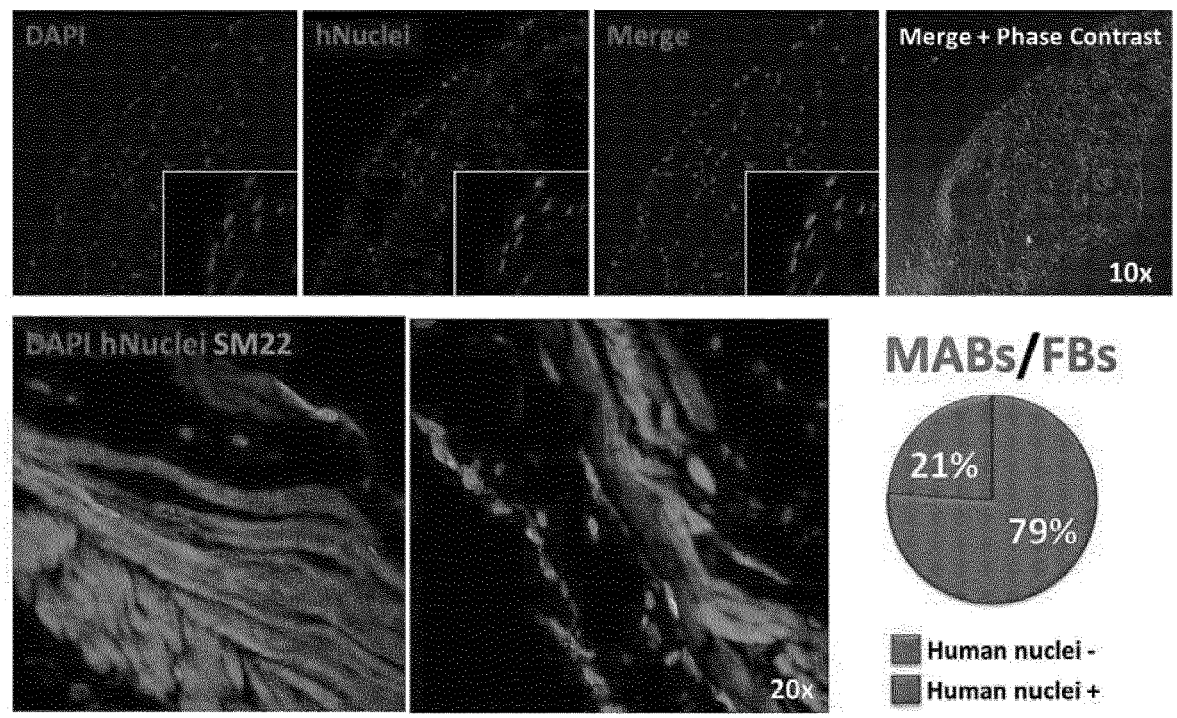

FIG. 12: Positive effect of FBs on the human MABs engraftment in the ECM. Seeding hMABs and mFBs in a ratio of 85:15 showed maintenance of cell proportion after 5 days in culture while 70:30 ratio led to a higher fibroblast proliferation during the culture with a resultant 50:50 ratio after 5 days. Cell proportion was determined with human nuclei staining; hMABs expressed skeletal muscle marker SM22 underlying muscle differentiation commitment.

Figure 13:
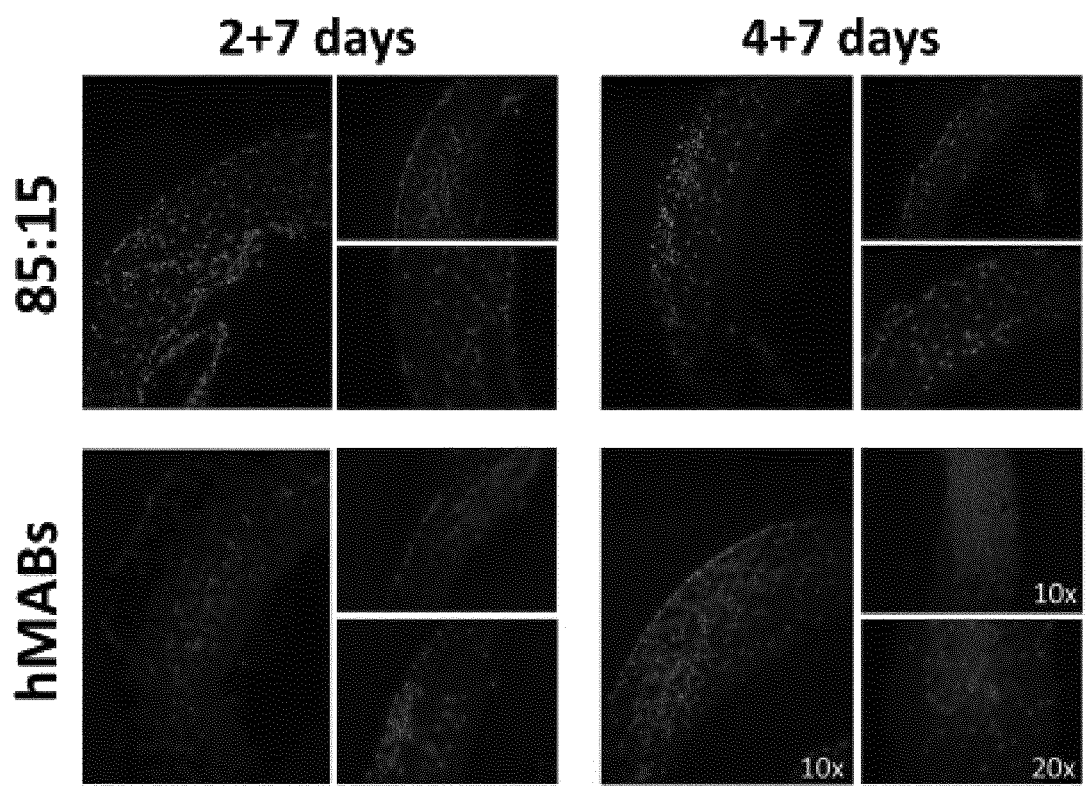

FIG. 13: Optimization of in vitro cell-seeding and culture conditions for mesoangioblasts and fibroblasts cultured on decellularized rat scaffold by varying proportions and culture conditions (days in proliferating medium+days in differentiating medium).

Figure 14:
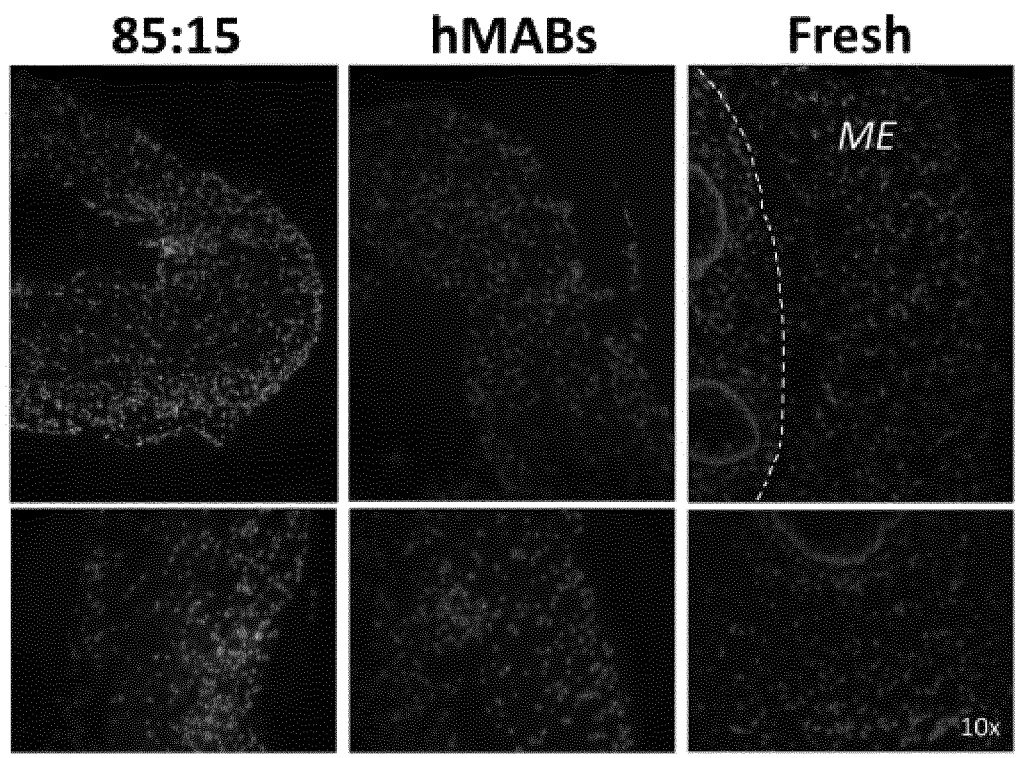

FIG. 14: Optimization of in vitro cell-seeding and culture conditions for mesoangioblasts and fibroblasts cultured on decellularized rat scaffold. An 85:15 mixture is compared with hMABS alone and the muscular layer of a fresh rat oesophagus.

Figure 15:
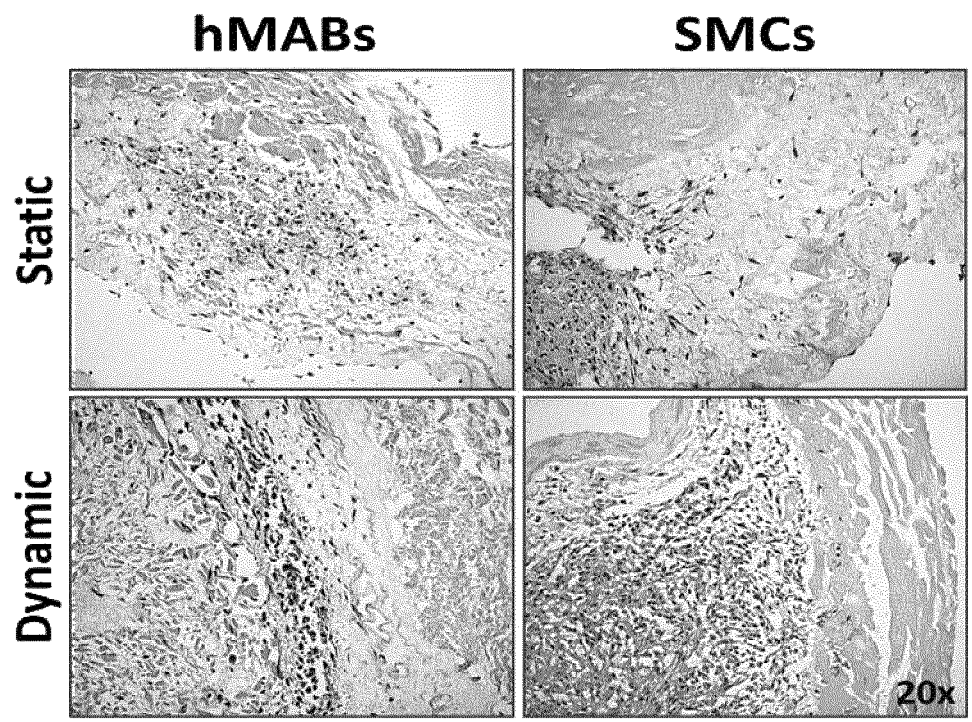
Figure 16:
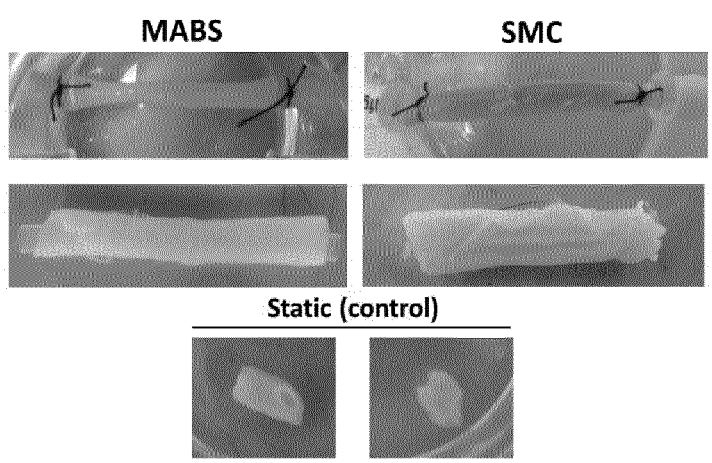

FIGS. 15 and 16: In vitro cell seeding experiments in decellularized rabbit oesophageal scaffold. Cell distribution and migration were compared in dynamic vs. static culture of hMABS alone and Smooth Muscle Cells (dog origin)

Figure 17:
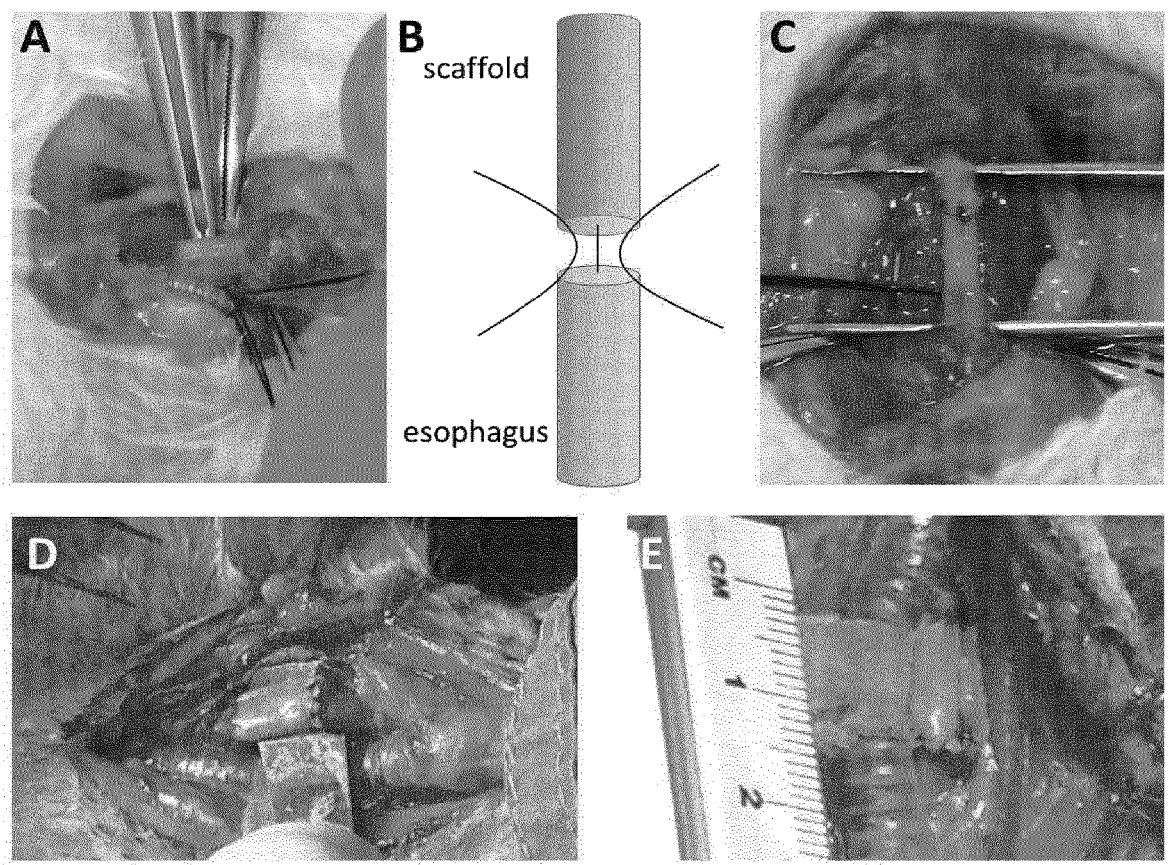

FIG. 17: Optimization of orthotopic transplantation of unseeded acellular scaffold from rat and rabbit donor animals into rat and rabbit models respectively. The original oesophagus was exposed reflecting thyroid lobes and muscles and a segment of oesophagus (between 1 and 2.5 cm, depending on the animal model) removed (FIG. 17A). Then distal and proximal anastomoses were performed (FIG. 17B) to connect both ends of the scaffold to the existing oesophagus (rat, FIG. 17C; rabbit, FIG. 17D,E).

Figure 18:
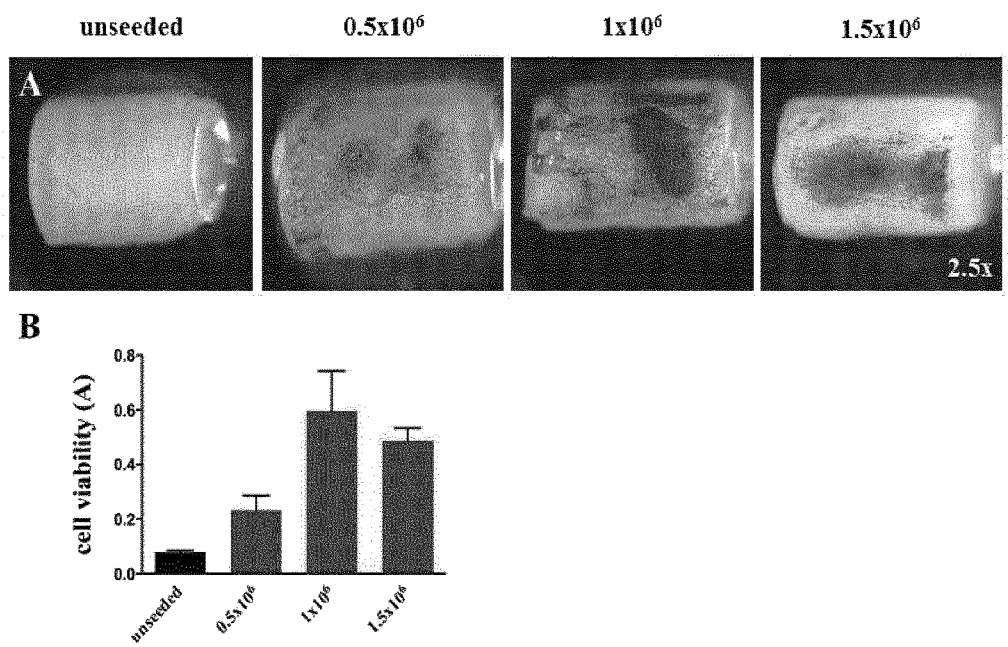

FIG. 18: MTT cell viability assay. A) Images of rat oesophageal scaffolds seeded with different hMABs densities. Cell number was detected indirectly measuring purple formazan production after 24 h; B) Quantification of cell viability through Absorbance reading of formazan extracted from seeded scaffold.

Figure 19:
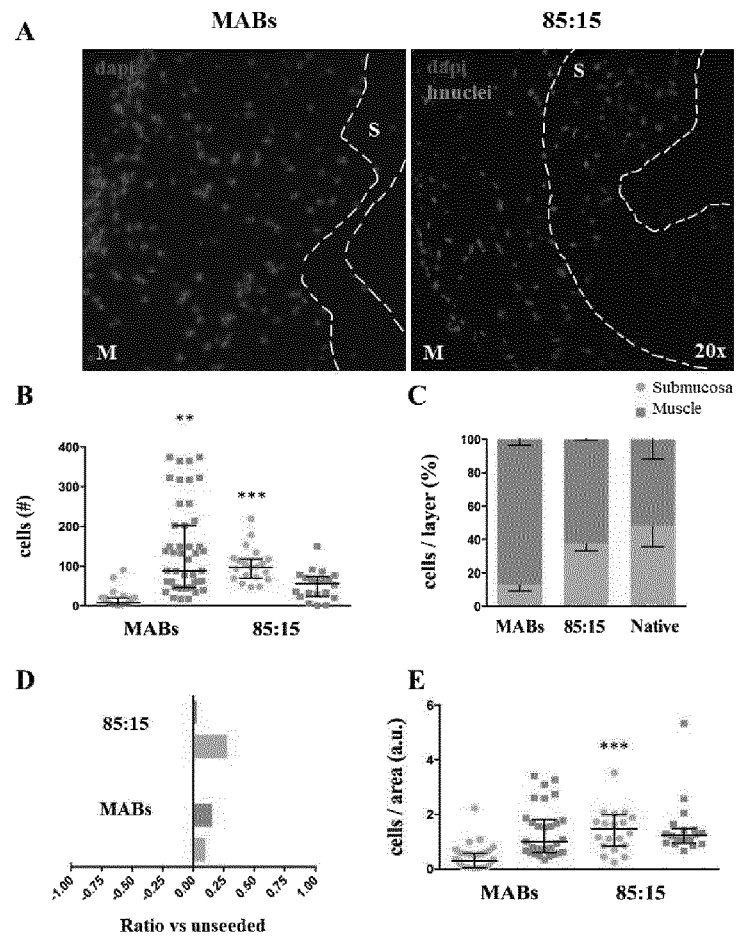

FIG. 19: A) representative images of hMABs- or co-seeded scaffolds after 9 days of dynamic culture; 85:15 sample stained also for hnuclei; B) representative cell number per field in each layer counted in random pictures of stained sections ($p<0.01$ and *$p<0.001$); C) distribution of cells between layers expressed as percentage in respect to the total number of cell engrafted in each condition; D) ratio between the area of seeded scaffold layers in respect to unseeded control (expressed at 0); E) representative cell density per layer calculated from cell number and area covered by the later in random pictures (M: muscle; S: submucosa).

Figure 20:
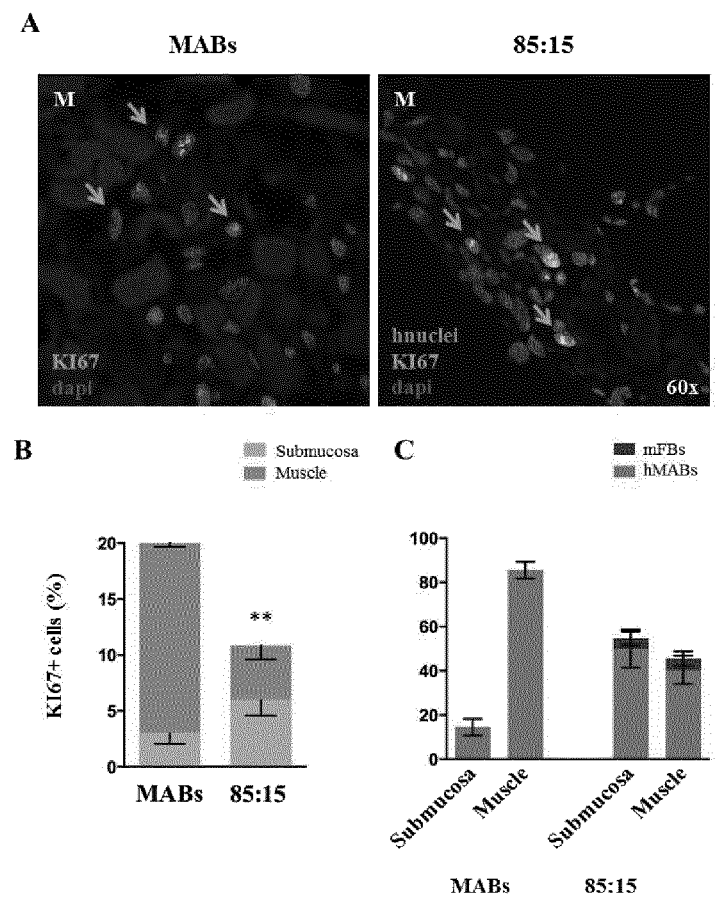

FIG. 20: A) representative pictures of KI67$^+$ cells. Human cells (85:15) marked also for hnuclei; B) percentages of KI67$^+$ cells after 9 days of dynamic culture in respect to the total number of cells counted in each layer of random pictures (**$p<0.01$); C) distribution of KI67$^+$ cells between layers, expressed as percentage, and contribution of mFBs (M: muscle).

Figure 21:
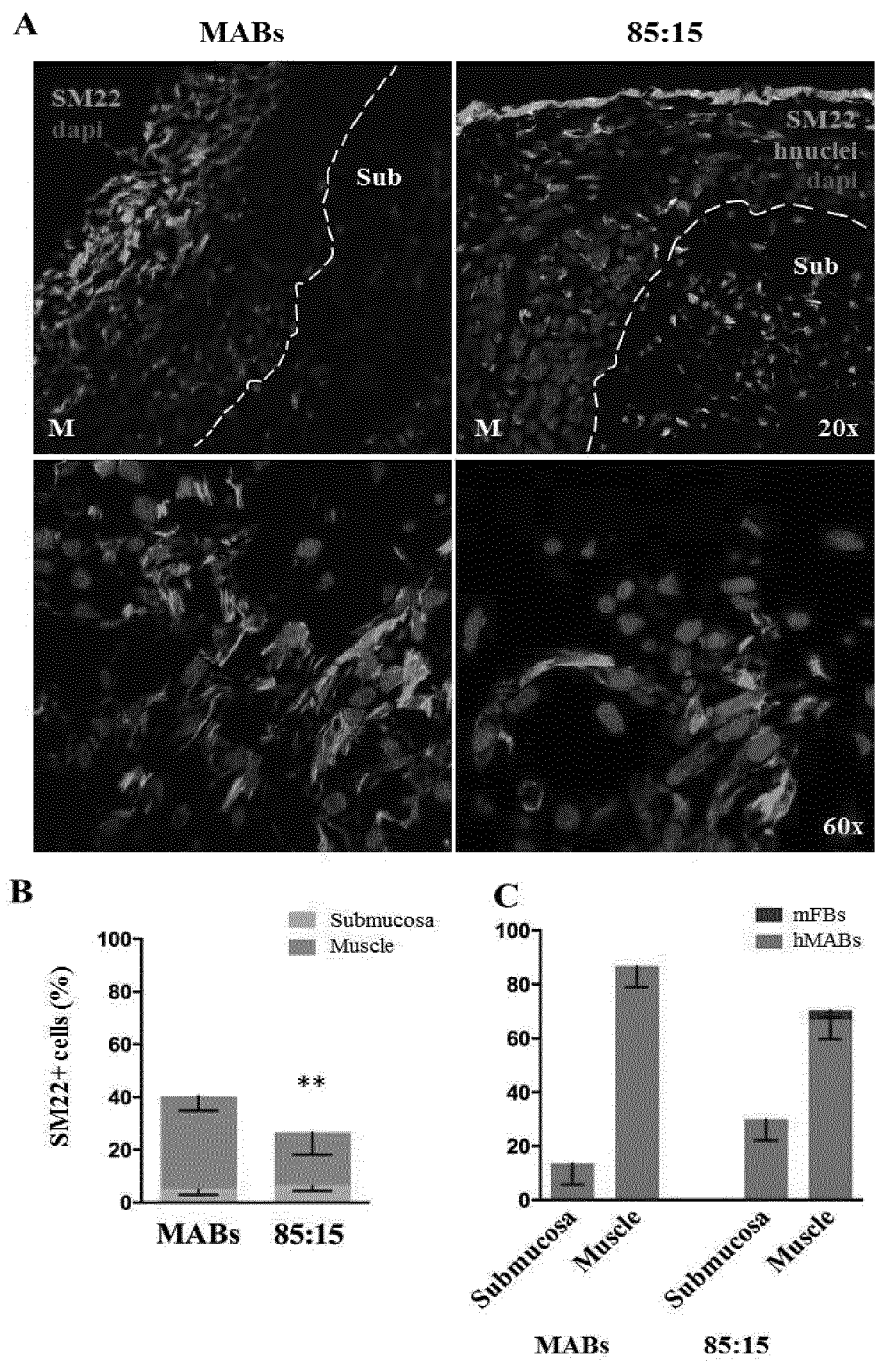

FIG. 21: A) representative pictures of SM22$^+$ cells. Human cells (85:15) marked also for hnuclei; B) percentages of SM22$^+$ cells in respect to the total number of cells counted in each layer of random pictures (**$p<0.01$); C) distribution of SM22$^+$ cells between layers, expressed as percentage, and contribution of mFBs (M: muscle; S: submucosa).

Figure 22:
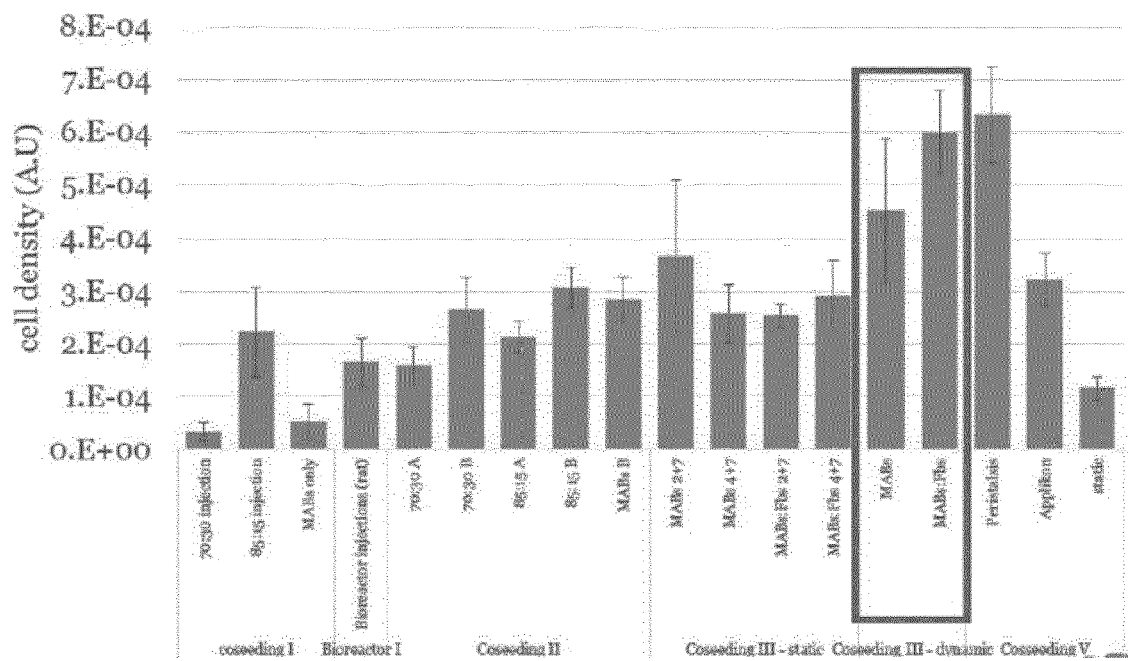

FIG. 22: comparison of cell density achieved using co-culture vs MABs alone—the results demonstrate the superiority of co-culture.

Figure 23:
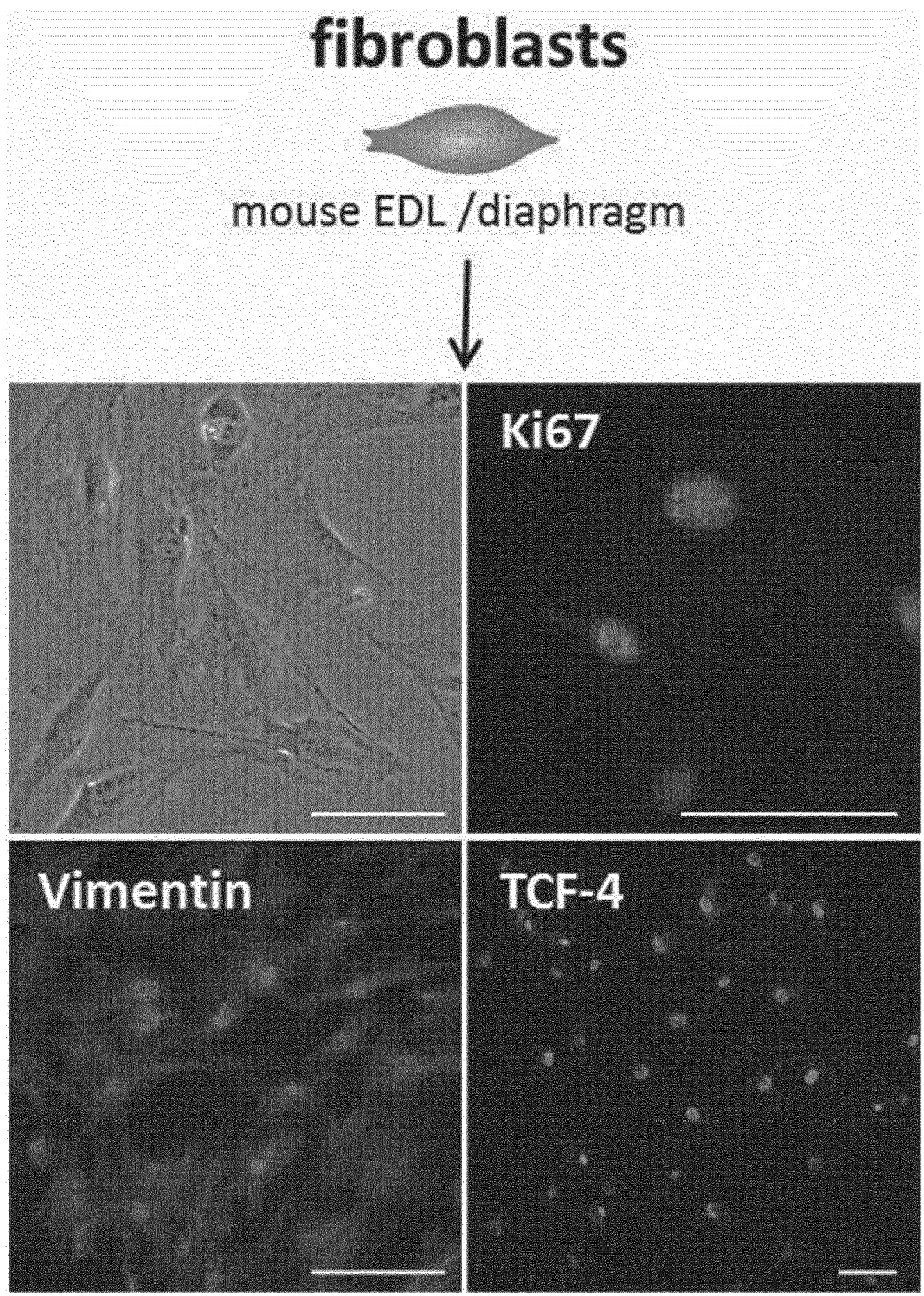

FIG. 23: Mouse fibroblasts (mFB) isolated from mouse hind limb skeletal muscles presented characteristic morphology after in vitro expansion (Ki67 staining for proliferation) and were positive for typical markers such as Vimentin and TCF-4 (bar: 100 μm).

Figure 24:
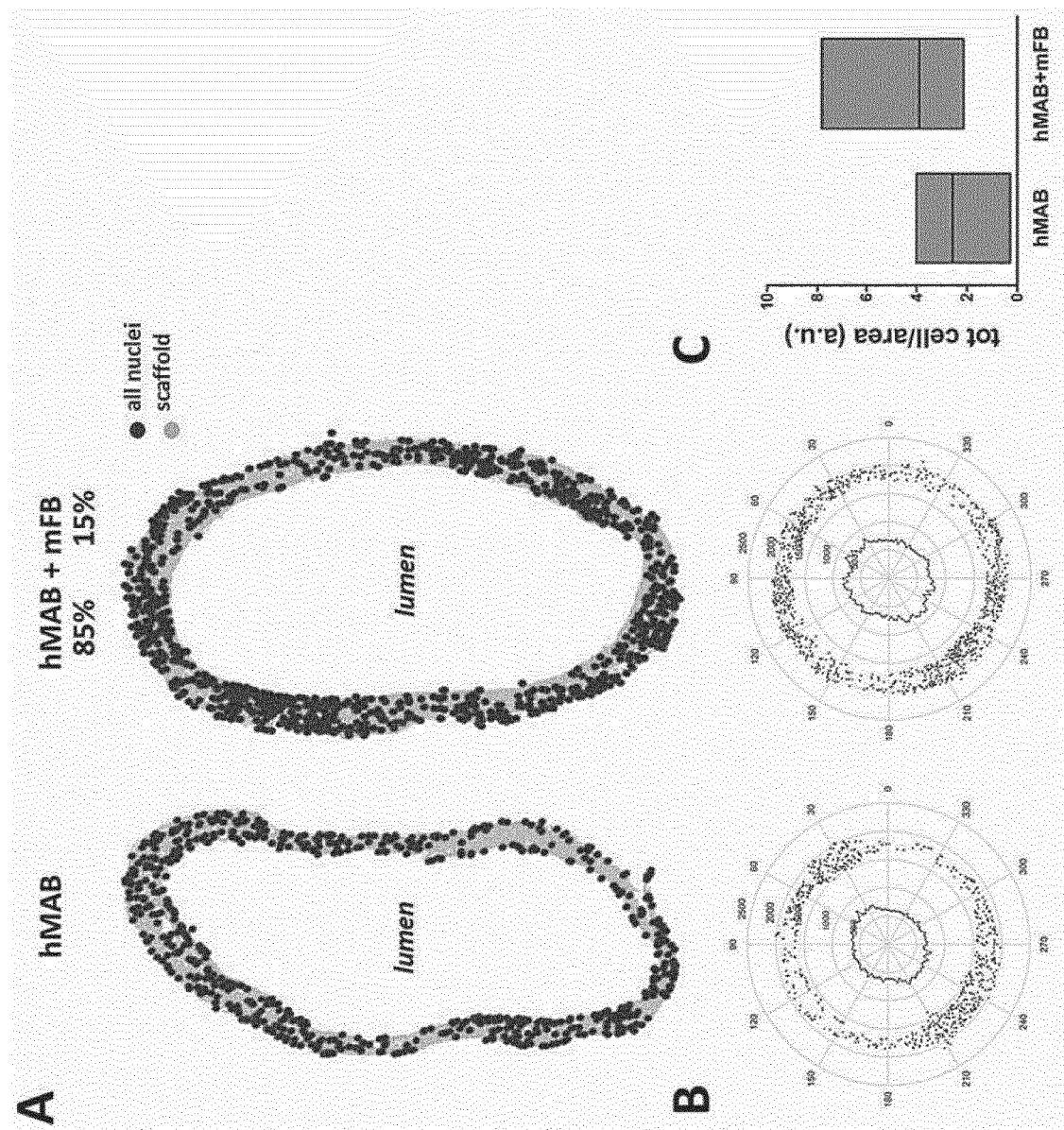

FIG. 24: A) Representative schematic distributions of all the cells within the scaffold after 6 days of static culture. B) Polar distribution of the same schematic distribution maps assuming a perfectly circular section. C) Total number of cells per area in hMAB only- or co-seeded scaffolds counted in random sections stained for DAPI and human Nuclei. n≥3.

Figure 25:
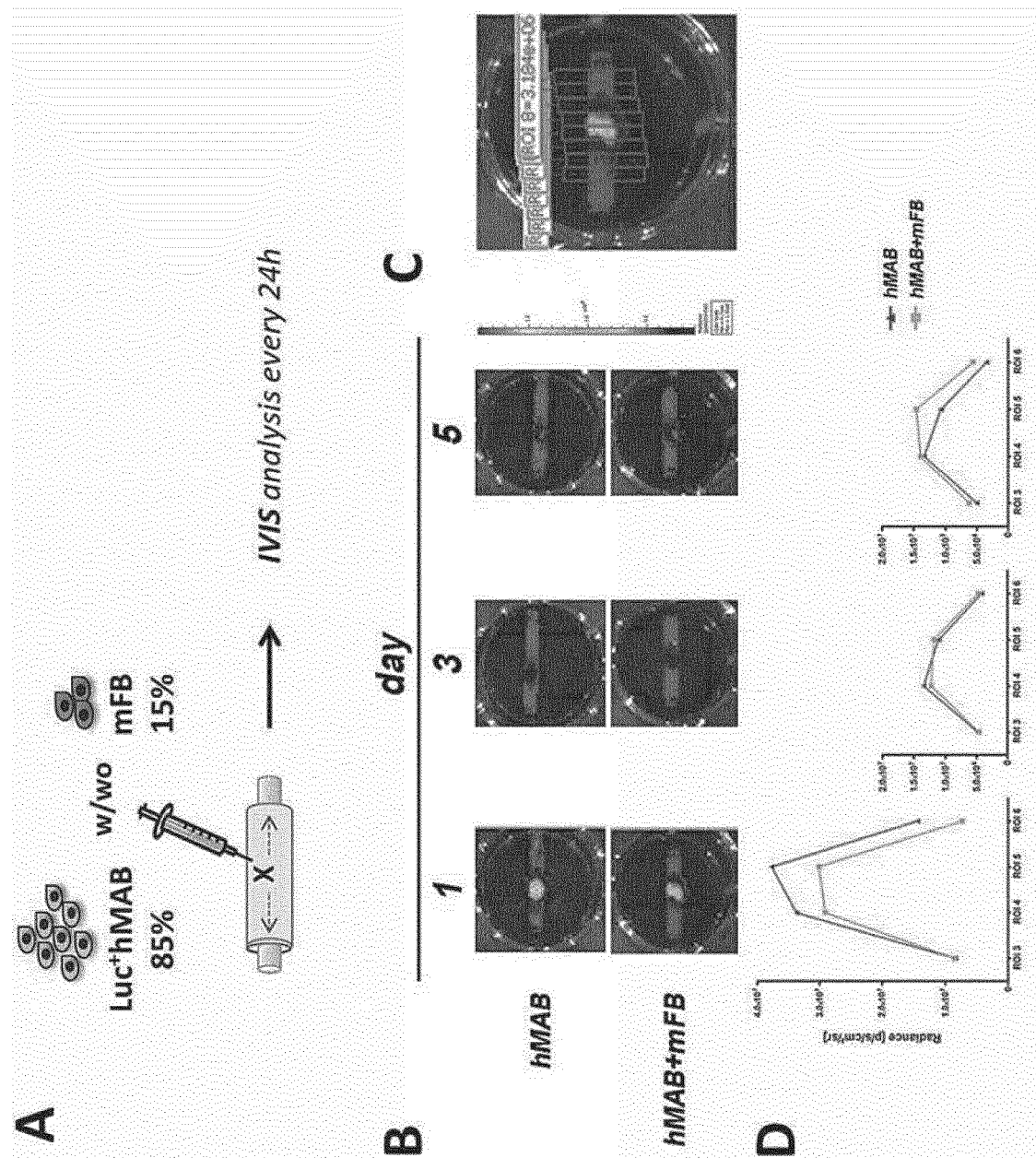

FIG. 25: A) Schematic representation of the study of the effect on the migration of hMAB when seeded with/without mFB. Luciferase$^+$ hMAB with/without wild type mFB were seeded in the centre of the tubular scaffold and bioluminescence measured with IVIS every 24 h for 5 days of static culture. B) Representative bioluminescence images showing Luciferase+ (Luc$^+$) cells in the scaffolds after 1, 3 and 5 days of culture. Images where analysed calculating the Radiance in 8 region of interests (ROIs) positioned from the centre of the injection point (C). Radiance measured in the ROIs 3 to 6 after 1, 3 and 5 days of culture.

Figure 26:
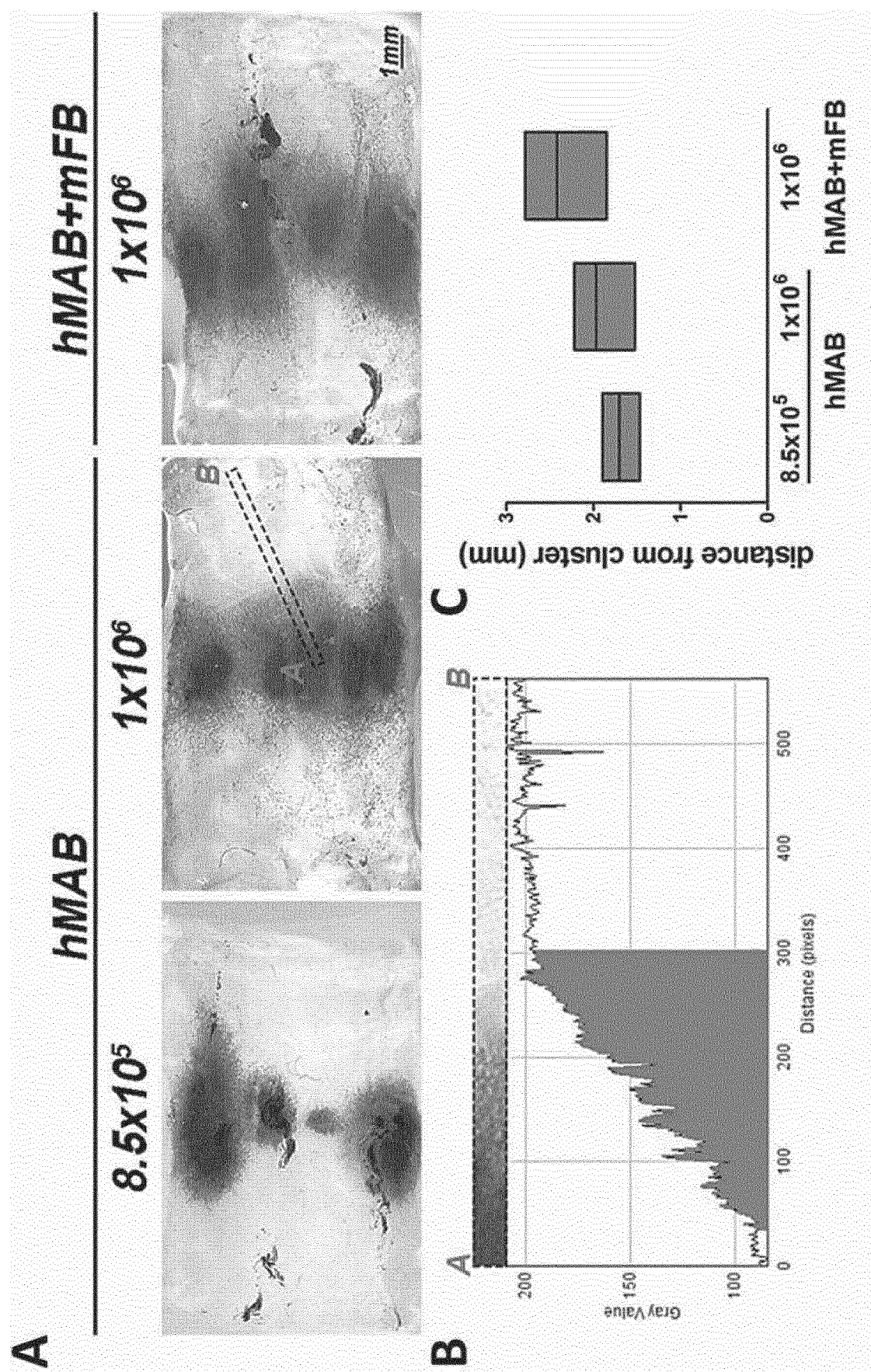

FIG. 26: A) Representative images of scaffolds seeded with 8.5×10$^5$ hMAB or 1×10$^6$ hMAB with/without mFB flat open and stained with MTT after 6 days of static culture. Cell migration from the injection points was analysed measuring the colour intensity (Gray Value) along 8 random lines draw radially from the centre of the cell clusters to the edge of the scaffold (segment A-B). B) Representative Gray value graph obtained from measuring the line A-B with the distance in pixels calculated between the 2 plateaus. C) Distance covered by the cells migrated from the injection point in mm.

Figure 27:
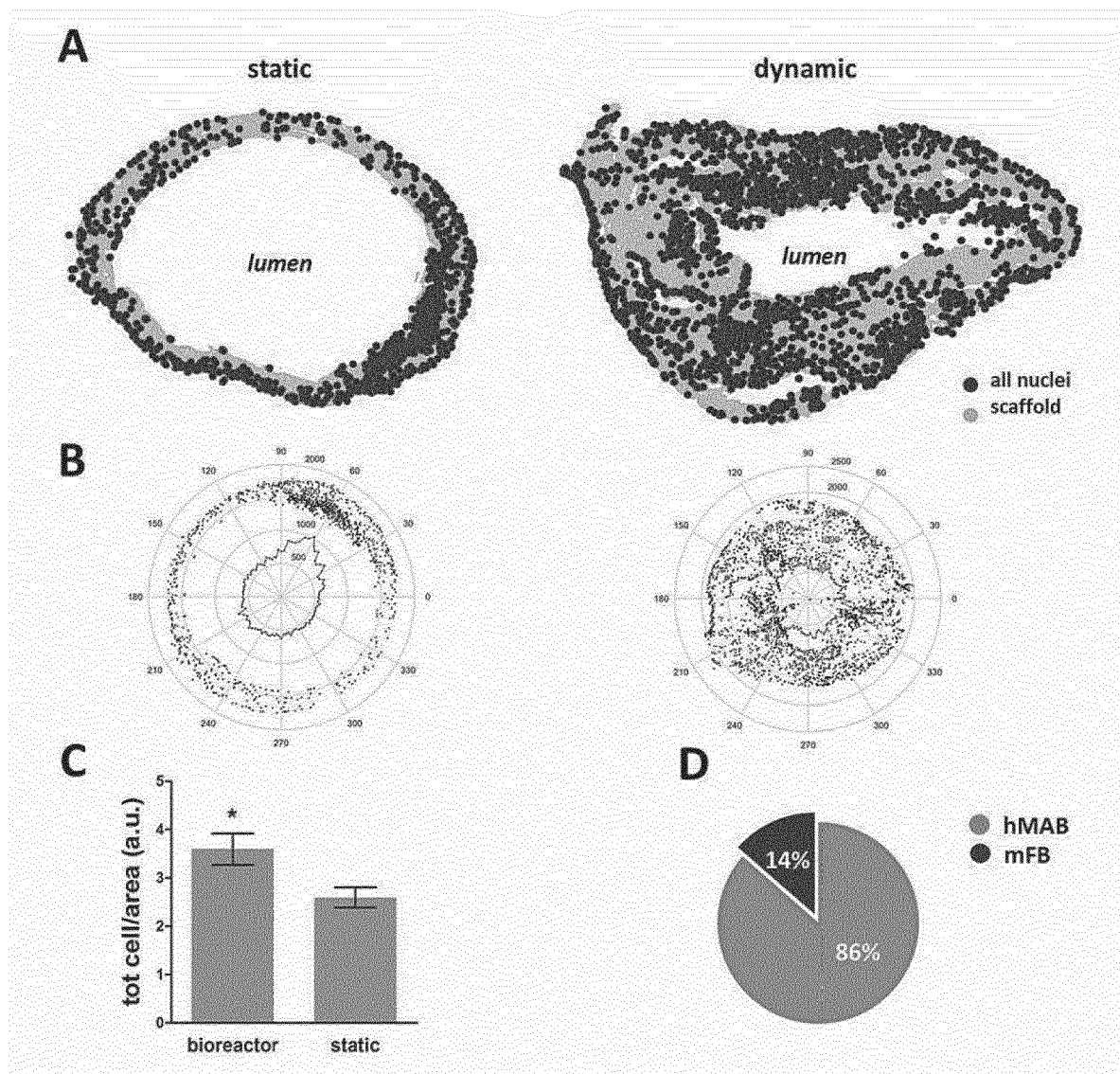

FIG. 27: A) Representative schematic distributions of all the cells within the scaffold after static or dynamic culture. B) Polar distribution of the same schematic distribution maps assuming a perfectly circular section. C) Total number of cells per area in scaffolds cultured in static or dynamic conditions counted in random sections stained for DAPI and human Nuclei (n≥3). D) Proportion of hMAB and mFB in scaffolds cultured in dynamic condition determined from cell counting in random sections stained for DAPI and human Nuclei (n≥3).

Figure 28:
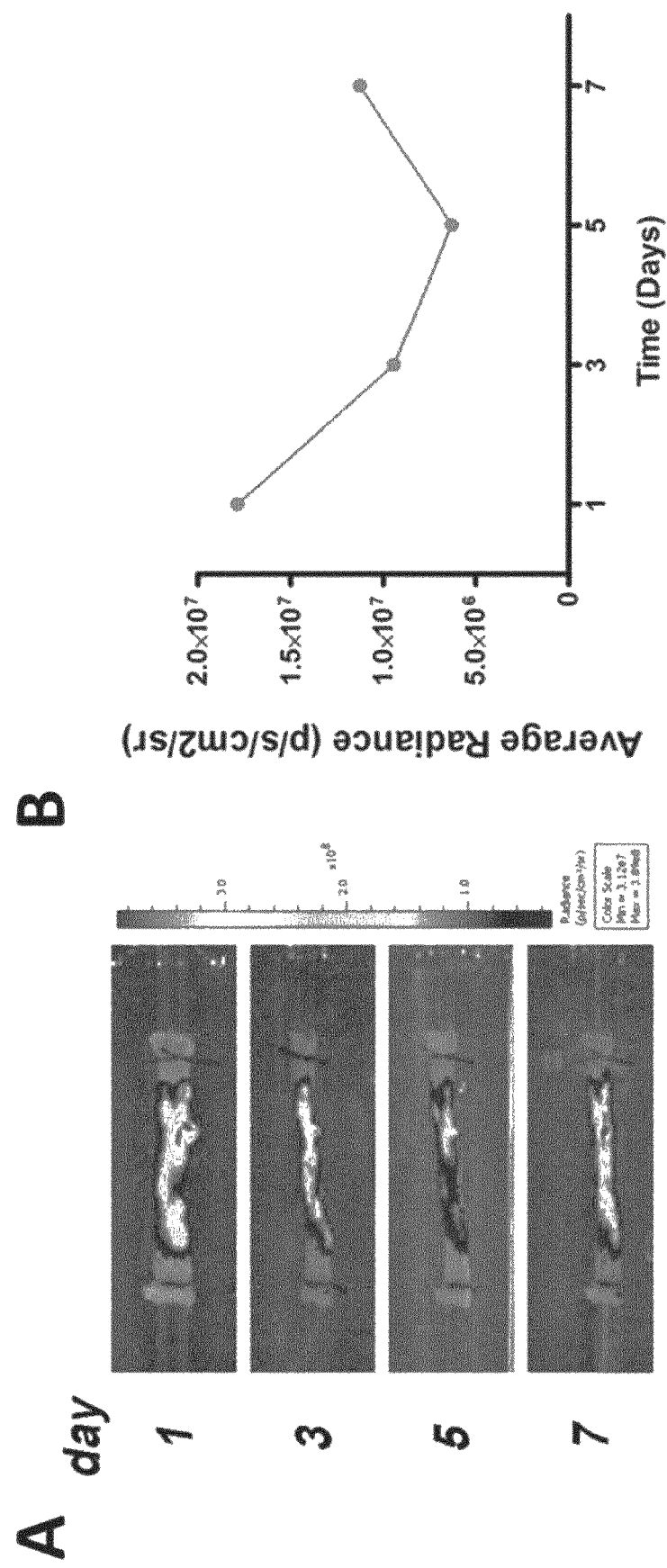

FIG. 28: A) Bioluminescence images of a scaffold co-seeded with Luc$^+$hMAB and mFB and cultured in the bioreactor for 7 days, showing the migration/distribution of the cells from the injection points. B) Radiance values calculated from the images collected at the different time points.

Figure 29:
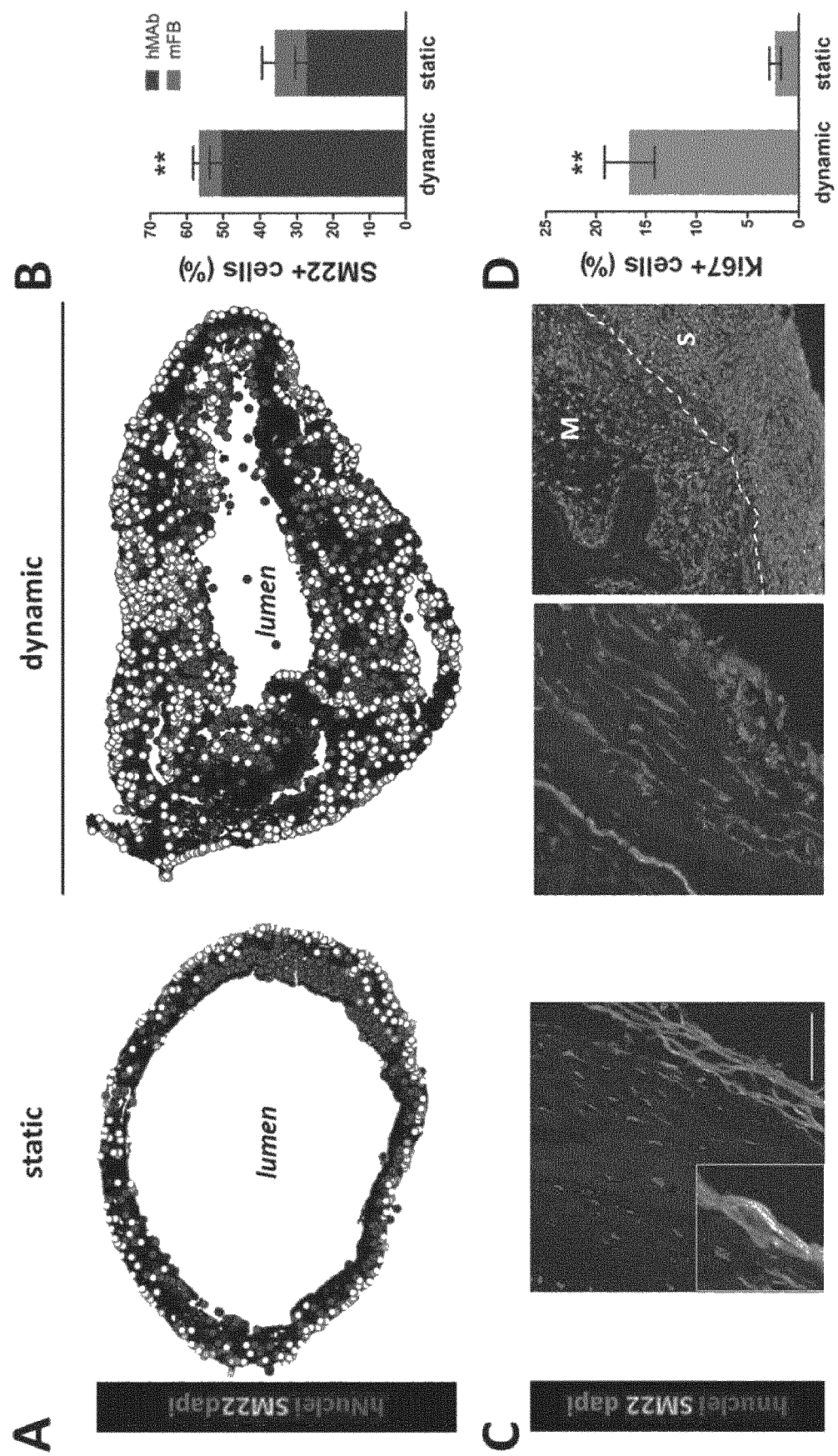

FIG. 29: A) Representative schematic distributions of all the cells within the scaffold (black) after static or dynamic culture. Cells were stained for human Nuclei and SM22; the figure also shows cells hNuclei$^+$SM22$^+$ and cells DAPI$^+$ (hNuclei$^-$SM22$^-$). B) Percentage of SM22$^+$ cells after static or dynamic culture counted in random images of different sections (n≥3) and the contribution of both hMAB and mFB to the total % ($p<0.01$). C) Representative images of staining for human Nuclei and SM22 (bar: 100 μm). D) Percentage of Ki67$^+$ proliferative cells after static or dynamic culture counted in random images of different sections (n≥3) ($p<0.01$).

Figure 30:
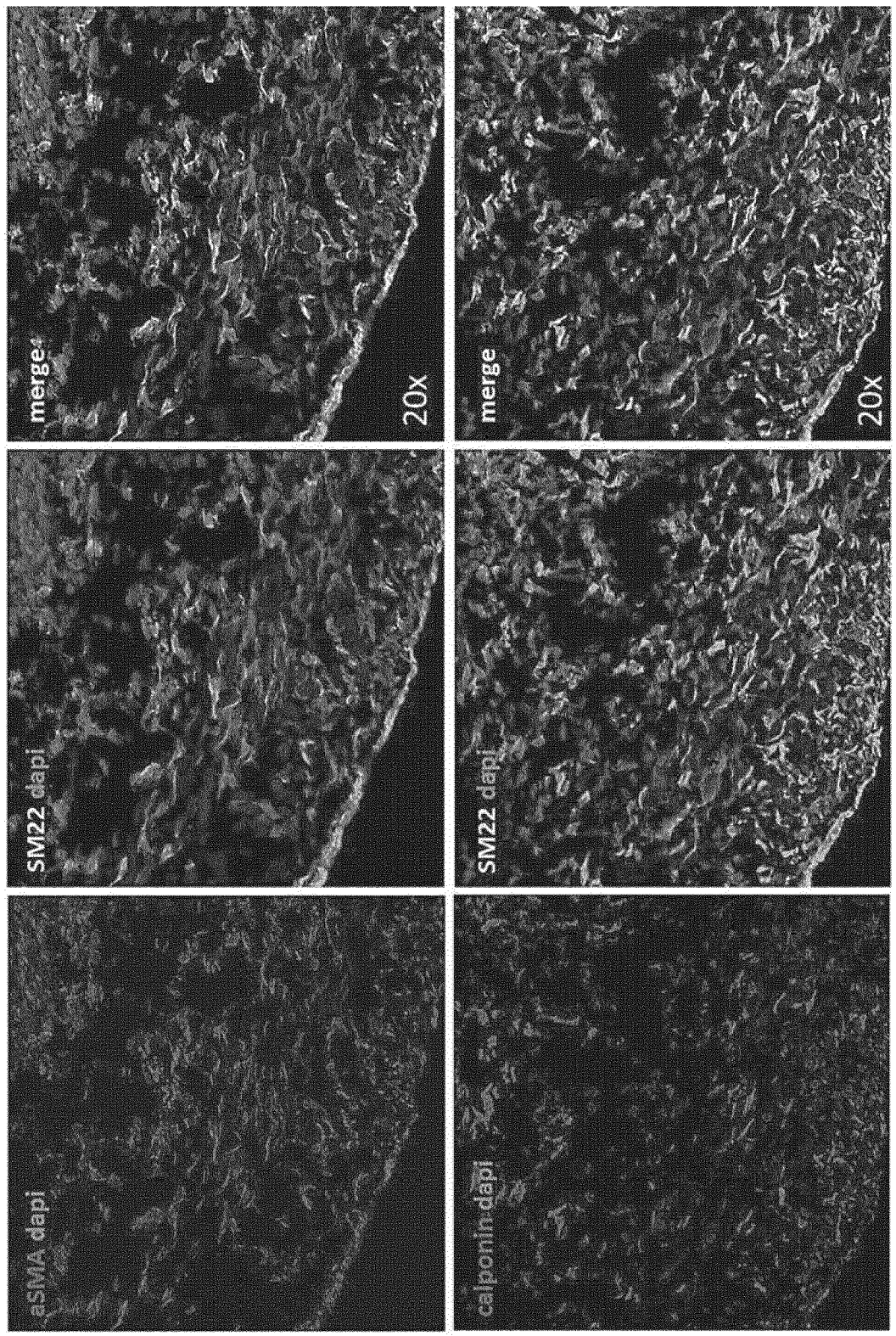

FIG. 30: Co-staining for αSMA or calponin with SM22 on scaffolds co-seeded with hMAB and mFB cultured in the bioreactor to assess the level of maturation of the smooth muscle cells.

EXAMPLES

Mesoangioblast Isolation and Characterisation.

Fetal mesoangioblasts (fMABS) were isolated from muscle tissue from human fetuses at 9-12 weeks of gestation. Specimens were plated on plates coated with diluted Matrigel and left in culture for 8 days. Cells migrated from muscle tissues were collected and expanded in culture for characterization. Cells were characterized at passage 4, 5, 6 and 7 of culture with immunofluorescence, FACS and differentiation potential towards smooth and skeletal muscle. For FACS analysis, cells were incubated with antibodies against CD31, CD34, CD44, CD45, CD56, CD90 and CD146. For differentiation potential, cells were incubated with low serum medium (skeletal muscle differentiation) and with the addition of TGFβ (for smooth muscle differentiation).

Establishment of Muscle Cell Lines

Six donor muscle biopsies (1 adult patient; 5 pediatric patients) were obtained with patient consent prior to procurement. Of the six biopsies, three primary mesoangioblast cell lines were successfully established and taken to passage 7 prior to differentiation into both skeletal and smooth muscle. Mesoangioblast cell lines were cryopreserved at each cell passage to establish a bank for future characterisation studies and re-culture. Mesoangioblast cell lines were established on collagen (placental-derived)-coated T25 flasks to allow direct comparison with procedures using matrigel coated perti dishes. An eight colour flow cytometric panel was established using the MACSQuant flow cytometer for phenotypic characterisation of mesioangiobalst cell lines at each passage. All antibodies were titrated and the panel validated for mesoangioblast characterisation.

Subsequently, two further adult muscle biopsies were procured after informed consent.

Primary mesoangioblast cell lines were successfully established on collagen coated culture flasks, using a procedure transferred from Prof Giulio Cossu at UCL. In total five cell lines were cryopreserved from passage 0 through to passage 7. Preliminary experiments were set-up to determine cell function and phenotype of thawed mesoangioblast cell lines in order to replicate the future clinical manufacturing process. Two cell lines at passage 3 were successfully thawed and re-cultured with no adverse effect on cell function, cell division and expansion and phenotype. Characterisation of skeletal and smooth muscle differentiation was investigated in two mesoangioblast cell lines by intracellular staining for both α-smooth muscle actin and myosin heavy chain by flow cytometry. Both antibodies have now been optimised and validated.

Derivation of Primary Fibroblast Cultures from Muscle Biopsies

Isolation and expansion of muscle derived fibroblasts was established from the same biopsies used in mesoangioblast isolation.

GMP-grade reagents (collagenase and neutral protease) were obtained for tissue digestion and successfully tested with one adult muscle biopsy. A fibroblast cell line was established and expanded to passage 4, adopting standard operating procedures Derivation of two cell lines from one biopsy allows more ready co-seeding of scaffolds to augment mesoangioblast cell attachment.

Epithelial Cell (EC) and Fibroblast Culture

EC and fibroblast culture (using MRC5 fibroblasts) was performed with ECs cultured on feeder layers of irradiated fibroblasts.

Data (not shown) demonstrates that rat oesophageal epithelia can be seeded effectively onto decellularized oesophagus.

Rat Oesophagus Decellularization.

Rat oesophagi were decellularized with detergent-enzymatic treatment (DET) consisting in luminal perfusion with continuous fluid delivery of de-ionised water at 4° C. for 24 h, 4% sodium deoxycholate at room temperature (RT) for 4 h and 50 kU/mL DNase-I in 1 M NaCl at RT for 3 h. Acellular scaffolds were stored for up to 1 month in PBS with 1% P/S at 4° C.

Cell Seeding

For cell seeding in the acellular scaffold, both fMABS and mouse fibroblasts (only for co-seeding experiments) were trypsinised between passage 5 and 7 and suspended in Matrigel growth factor reduced (GFR) diluted 1:2 or only medium and kept on ice. Scaffolds were canulated with an NG tube to allow easier access and handling for seeding. Cells were injected using an insulin syringe and performing multiple injections of about 5 µL each to cover as many areas of the oesophageal scaffold as possible. Cells were injected at a density of $10^6$ cells/5 mm length directly into the muscle layer of the matrix, using a stereomicroscope placed in a sterile hood (FIG. 1). Alternatively, cells suspended in Matrigel GFR diluted 1:2 or in medium were seeded on the surface of the scaffold.

Depending on the seeding condition tested and the outcomes, seeded scaffolds were optionally:
  cultured as tubular matrices in static condition in multiwell plates with proliferating or differentiating media,
  opened longitudinally, cultured as flat matrices in static condition in multiwell plates with proliferating or differentiating media (FIG. 2),
  sutured to plastic or glass arbours as tubular matrices and placed in bioreactor for 24 h of static culture and subsequent 6-7 days of dynamic culture.

Engineered oesophagi cultured in static or dynamic conditions were fixed with formalin at 6-7 days of culture and processed for histological and immunofluorescence analysis.

Bioreactor

Dynamic culture was typically performed using a Bioreactor supplied by Applikon® Biotechnology, suitably adapted. The Bioreactor consisted of two components: an autoclavable reservoir equipped with sensors and stirrer; a controller monitoring pH, temperature, stirrer speed, foam level and supporting tubing pumps. In addition, a PC was installed as interface.

Oesophageal seeded-scaffolds were placed inside custom chambers made of glass (although other materials could be used similarly) which allowed both sterilisation and visual monitoring of the sample within. Each edge of the scaffold was sutured to a glass rod in a sterile dish inside a tissue culture hood. Then, rods and scaffold were gently trailed through the glass chamber until both rods were protruding out of each end. Caps, together with washers and O-rings, were then connected and closed. On the other end, tubings equipped with luer loks linked the rod's open ends to the reservoir to ensure medium circulation. Finally, scaffold-hosting chambers were placed inside a standard incubator.

In order to establish a pulsatile flow, a dedicated pump (iPump) was utilised.

In use, seeded oesophageal matrices seeded with fMABS were mounted into the autoclavable culture chambers (see e.g. FIG. 3) and left in static culture for 24 h in proliferating medium. Then the medium was removed from the chamber (both external and inner compartments), changed with differentiating medium and the chamber was connected to the Applikon bioreactor with sterile tubing and connectors to start dynamic cultured (FIG. 4). The bioreactor allowed control of reservoir temperature, $O_2$ and $CO_2$ pressure in the medium, flow rate, external/inner compartment medium recycling.

Transplantation of the Engineered Oesophagi in the Omentum

After cell seeding, under anaesthesia, 5 mm tubular scaffolds were implanted into the abdominal cavity of nude mice and wrapped with the omentum using absorbable sutures. Scaffolds were implanted with the NG tube in the lumen to avoid matrix collapse and maintain the oesophageal architecture (FIG. 5). Animals were sacrificed at 2 and 4 weeks after implantation and scaffolds harvested and fixed for histology.

Histological and Immunofluorescence Analysis

Tissue samples and cell cultures were fixed in 10% neutral buffered formalin solution in PBS at 4° C. for 24 h (tissues) or 10 min (cells) then washed in distilled water (dH2O). Tissues were dehydrated in sucrose solution and froze in liquid nitrogen for cryosectioning. 7 µm sections and cells fixed in plates were stained with Haematoxylin and Eosin (H&E) or immunostained for Alkaline Phosphatase (AP), NG2, PDGFRbeta, Myosin Heavy Chain (MyHC), Myogenin, alpha Smooth Muscle Actin (aSMA), SM22, human nuclei, Ki67, CD68 and MyoD. Samples were then incubated with fluorescent secondary antibodies, counterstained with DAPI and mounted with aqueous mounting medium.

Example 1—Fetal MABS Characterization

Fetal MABS showed comparable morphology, features and marker expression with adult MABS. FACS analyses detected low levels of CD31, CD34, CD45, CD90 (0-1%), high levels of CD44 (97-100%) and variable levels of CD56 and CD146 (0-25%). In culture with proliferating medium, fMABS were positive for AP reaction and NG2 staining, two classic markers of MABS (FIG. 6). When incubated with skeletal muscle differentiating medium, cells were able to fuse and form mature myotubes positive for MF20 and expressing the nuclear marker myogenin (MyoG). fMABS also demonstrated differentiation ability towards smooth muscle phenotype when cultured with low serum medium added enriched with TGFβ cytokine. After 6 days in smooth muscle differentiating medium cells expressed typical smooth markers such as SM22 and aSMA.

Example 2—Cell Seeding Optimization in the Acellular Oesophageal ECM

Oesophageal acellular matrix seeding was performed comparing cell delivery in Matrigel or medium to understand vehicle's effect on cell survival and engraftment. In addition, microinjection versus superficial seeding comparison was evaluated analysing cell adhesion and migration into the scaffold after 24 and 48 hours of static culture. Fetal MABS delivered in Matrigel either through microinjections and surface seeding in rat acellular oesophageal scaffolds showed cell adhesion and survival after 24 and 48 h. Cell adhesion on the surface of the matrix was more efficient than cell engraftment within the matrix in microinjected samples; however cell number increased with time in the case of microinjected matrices highlighting higher cell proliferation (FIG. 7). Cells seeded only with medium displayed lower engraftment and proliferation, with no substantial changes between 24 and 48 h of static culture. These data helped improve the comprehension of Matrigel vs medium and seeding technique effects on cell survival and proliferation into the acellular matrix.

Example 3—Co-Seeding of fMABS and mFBs in the Acellular Scaffold

Co-seeding experiments were performed to establish fibroblast (FB) effect on cell survival and migration inside the matrix when seeded together with fMABS. We microinjected fMABS combined with mouse FBs in a ratio of 85:15 and 70:30 or fMABS alone as a control, for a total cell density of $1 \times 10^6/5$ mm scaffold length. Samples were then cultured in static condition for 5 days. Cryosections of seeded scaffolds stained with DAPI showed a considerable number of cells and better cell distribution in co-seeded scaffolds compared to fMABS alone seeded samples, indicating a positive effect of FBs on fMABS engraftment in the ECM (FIG. 8). Furthermore, the best ratio of fMABS and mFBs seemed to be 85:15, displaying an evident higher number of cells inside the matrix. These data will be completed with additional analyses to identify fMABS and mFBs in the seeded samples and their marker expression specification after 6 days in co-culture. In addition, exact number of cells per area will be determined in random pictures.

Example 4—Dynamic Culture with Bioreactor

In parallel with co-seeding experiments, dynamic culture experiments were performed using a bioreactor and two different culture chambers for hollow organs. The chambers were characterised by similar features: inner and external chamber with separate flow, autoclavable, connectable with medium reservoir through silicon sterile tubings and connector. Nevertheless, preliminary experiments highlighted some issues related to contamination of the scaffold, maintenance of a constant and tuneable medium level inside the chamber, and suturing the tubular scaffold to the harbour. For these reasons, after initial attempts, dynamic culture experiments were conducted using a custom made glass chamber described above.

Fetal MABS were microinjected into the oesophageal acellular scaffold and the construct was then sutured to the two glass inserts that allow separating the inner and external compartment of the chamber. The culture chamber was assembled, connected to the bioreactor and the reservoir and finally filled up with proliferating medium in both compartments. The chamber was incubated 6 h in static condition before starting the medium flow in the inner chamber for dynamic culture (FIG. 9). After 24 h of culture, the medium was changed from proliferation to differentiation medium both in the chamber and the reservoir. The dynamic culture was stopped after 6 days with a complete medium change at 3 days of culture. From preliminary analysis of cryosections obtained from the dynamic cultured seeded scaffold there was an evident cell engraftment and proliferation inside the matrix (FIG. 9). The dynamic cultured samples seemed to improve cell migration and a better homogeneous distribution within the scaffold, compared to preliminary evidences. Furthermore, the bioreactor set up used in this experiment improved the overall culture success avoiding contaminations, allowing a better flow control, temperature control, oxygenation of the medium and scaffold handling.

Example 5—Omental Implantation of Seeded Scaffold

To study acellular scaffold vascularization and remodelling in vivo, MABS seeded tubular scaffolds were implanted in the omentum of immunocompromised mice as a pre-vascularization step before future orthotropic transplantations.

After 2 and 4 weeks from transplantation, human MABS were identified in the scaffold with human nuclei staining (FIG. 10A). H&E and immunofluorescence analyses showed cell migration from the host (hnuclei negative) indicating a cell homing activation by the implanted ECM. Histology also highlighted modest matrix remodelling after 2 weeks from transplantation with oesophageal ECM layers that were still recognizable. On the other hand, matrix remodelling was more evident 1 month after transplantation with loss of original structures. Human cells were fewer after 1 month time point when counted in respect to analysed area (cm$^2$) (FIG. 10B). When analysed with a proliferation marker (Ki67), about 5% of total number of cells were proliferating human MABS whilst a remaining 9% was negative for this marker at 2 weeks post-transplantation (FIGS. 10C and D). After 1 month, no proliferating cells were found within the scaffold. These preliminary data indicate that 2 weeks seems to be a good compromise for this in vivo step to obtain initial pre-vascularization (evidenced by presence of small new vessels in H&E stained sections) and limited matrix remodelling preserving original ECM organisation. Samples were characterised for presence of macrophages (CD68+ cells), smooth muscle cells (aSMA+ cells) and MyoD (skeletal muscle precursor cells). Human MABS were negative for smooth and skeletal muscle markers indicating loss of function of these cells that stopped proliferating and differentiating after few days from transplantation. Further analyses and additional experiments need to be performed to understand cell behaviour and to improve their engraftment and activation. Macrophages were found within the scaffold homogenously distributed at both the time points, supporting the remodelling process ongoing in the scaffold by host cells.

Example 6—Analyses of Previous Cell Seeding Experiments with Decellularized Rat Scaffolds Mesoangioblasts (MABs) injected into the rat oesophageal acellular scaffold and cultured for 24 h in proliferating medium followed by 5 days of differentiation medium (towards skeletal muscle). From preliminary analysis (DAPI staining) of cryosections obtained from the cultured scaffold there was an evident cell engraftment and proliferation inside the matrix (FIG. 11A,B). Deeper analyses highlighted cell distribution and migration stimulated and improved by the dynamic culture condition (H&E, FIG. 11C,D). Cells also displayed initial commitment towards skeletal muscle differentiation as determined with MyoD staining, a specific marker for skeletal muscle precursor cells (FIG. 11E,F).

As noted previously (FIG. 8), when MABs were co-injected with mouse fibroblasts (mFBs) in a ratio of 85:15 and 70:30 and cultured for 5 days in static conditions a considerable number of cells engrafted and there was improved cell distribution compared to MABS alone seeded samples, indicating a positive effect of FBs on the human MABs engraftment in the ECM (FIG. 12). Subsequent analyses revealed that seeding hMABs and mFBs in a ratio of 85:15 showed maintenance of cell proportion after 5 days in culture (FIG. 12), while 70:30 ratio led to a higher fibroblast proliferation during the culture with a resultant 50:50 ratio after 5 days. Cell proportion was determined with human nuclei staining (FIG. 12). Furthermore, hMABs expressed skeletal muscle marker SM22 underlying muscle differentiation commitment.

Example 7—Optimization of In Vitro Cell-Seeding and Culture Conditions for Mesoangioblasts and Fibroblasts Cultured on Decellularized Rat Scaffolds The best co-seeding condition of hMABs:mFBs (85:15) was used to optimize culture condition in comparison with hMABs alone. Rat scaffolds injected with 85:15 co-seeding or only hMABs were cultured for 2 or 4 days in proliferating medium followed by 7 days (2+7 and 4+7 days respectively) in differentiating medium containing TGFbeta to induce smooth muscle differentiation. Scaffolds were cultured in static and dynamic settings. No distinct differences were highlighted from DAPI staining of static cultured samples between 2+7 and 4+7 culture conditions (FIG. 13).

When compared to hMABs alone, both 2+7 and 4+7 conditions for 85:15 seeding showed better engraftment, distribution and cell orientation within the scaffold (FIG. 13). Dynamic culture of co-seeded or only hMABs seeded scaffolds for 2+7 evidenced remarkable cell engraftment and proliferation in respect to static conditions (FIG. 14). The number of cells detected after 2+7 days of culture was more similar to the muscular layer of a fresh rat oesophagus compared to all previous static culture experiments (ME: muscularis externa, FIG. 14).

Example 8—In Vitro Cell Seeding Experiments in Decellularized Rabbit Oesophageal Scaffold hMABs alone were seeded in decellularized rabbit oesophageal scaffold and cultured in static and dynamic culture for 7 days. Smooth muscle cells (dog origin) were used as control in parallel experiments (FIG. 15). The rabbit scaffold seeding confirmed better cell distribution and migration when comparing dynamic culture with static, despite seeding hMABs alone. SMC seeded samples showed high cell engraftment and survival, but lower cell migration from the site of injection (FIG. 16). hMABs displayed homogenous distribution in all scaffold layers and orientation along pre-existing muscle fibres (H&E, FIG. 16).

Example 9—Optimization of Orthotopic Transplantation of Unseeded Acellular Scaffold from Rat and Rabbit Donor Animals into Rat and Rabbit Models Respectively The procedure for orthotopic transplantation of acellular oesophageal scaffolds was further optimised. Segments of decellularized matrices were implanted without previous cells seeding into rats and rabbits to define steps and conditions for future engineered construct transplantations in vivo. The procedure was developed for both rat and rabbit animal model. This consists in exposing the original oesophagus reflecting thyroid lobes and muscles, remove a segment of oesophagus (between 1 and 2.5 cm, depending on the animal model) and pass a NG tube to help stabilizing and identifying oesophagus during anastomoses (FIG. 17A). Then distal and proximal anastomoses were performed (FIG. 17B) to connect both ends of the scaffold to the existing oesophagus (rat, FIG. 17C; rabbit, FIG. 17D,E).

These experiments highlighted that the constructs of the invention were capable of (i) effective suturing without immediate leakage, (ii) good tensile/stress properties, for food intake, (iii) excellent biocompatibility.

Example 10—Optimization of Cell Seeding Density

In order to establish the amount of cells necessary to obtain successful engraftment, different human mesoangioblast (hMABs) densities were tested using MTT viability assay and imaging, which allowed visualisation of the engrafted cells and their indirect quantification. Viable cells metabolize the substrate provided (MTT) and produce a visible colour changed product (formazan) that can be extracted and quantified by absorbance reading. Scaffold segments were seeded and incubated for 24 hr prior proceeding with the assay.

After a 4 hr incubation with MTT solution, formazan-positive cells were visible within the scaffold highlighting their migration from the injection site (FIG. 18A). Preliminary analysis of pictures suggested that injection of $1 \times 10^6$ cell/0.5 cm led to the most effective engraftment. This result was further confirmed quantifying the reaction product. Absorbance measurements confirmed that the concentration of formazan, which reflects the number of viable cells, was higher in this condition compared to the others (FIG. 18B).

Example 11—Investigation of Cell Distribution and Differentiation in all Scaffolds Cultured with the Dynamic System To enhance cell engraftment and distribution within the scaffold, a dynamic culture approach was used allowing continuous medium flow, favouring nutrient and oxygen exchange. As previously determined, hMAbs- and co-culture (hMABs and fibroblasts) seeded oesophagi were cultured 2 days in growth medium and 7 days in smooth muscle differentiation medium. TGFβ was provided fresh daily at a concentration of 2 ng/ml. As shown in FIG. 19A-B, after a total of 9 days of culture, the muscle layer of hMABs-seeded scaffold hosted a significantly higher number of cells compared to the co-seeded counterpart. The submucosa showed the opposite trend, being significantly more populated in the co-seeded scaffold than in the hMABs alone one.

In addition, using the co-seeding process, cells were more homogeneously distributed in co-seeded scaffolds in respect to hMABs-seeded samples, confirming previous experiments performed in static (FIG. 19C). Interestingly, at the end of the culture period, dimensions of all oesophageal layers resulted to be expanded in both conditions when compared to unseeded matrices (FIG. 19D). In particular, the muscle layer of hMABs-seeded scaffold resulted to be wider than the co-seeded counterpart. This increase in thickness, together with a higher number of engrafted hMABs, produced a resultant cell density comparable to 85:15 seeded scaffolds (FIG. 19E).

Proliferation analysis through detection of KI67+ cells (FIG. 20A) showed that the percentage of proliferating cells was significantly higher in the hMABs-seeded scaffold (24%) compared to the co-seeded one (10%). Notably, in the hMABs-seeded scaffold the highest percentage of proliferating cells (85%) was detected in the muscle layer whereas in the co-seeded scaffold KI67+ cells appeared to be more uniformly distributed as highlighted by cell density calculation (FIG. 20C).

In respect to the smooth muscle differentiation, the % of SM22+ cells was higher in the scaffold seeded with hMABs alone (40%) compared to the co-seeded one (FIG. 21A-B). In addition, as previously evidenced in static condition, the majority of differentiated cells distributed in the muscle layer in both hMABs-seeded (85%) and co-seeded scaffold (70%) (FIG. 21C).

Example 12—Choice of Scaffold

Analysis showed that supply of neonatal human donor tissue may be insufficient for demand. Decellularized animal-derived scaffolds were therefore tested alongside manufactured human cell-derived scaffolds.

When compared in vivo the decellularized porcine tissue remained intact whereas the manufactured human cell-derived scaffolds degraded, thus confirming the superiority of porcine tissue.

Example 13—Example Protocol for Generation of a Tissue-Engineered Oesophagus as an Autologous Therapy for Neonate 1. Harvest porcine oesophagus, place in storage solution and transport to GMP manufacturing site.
2. Decellularize using 2 (two) cycles of the DET protocol (water for 24 h at RT, Sodium Deoxycholate for 4 h at RT and DNase for 3 h at RT), irradiate the scaffold (to sterilise) and store in buffered solution.
3. Inject decellularized scaffold with mesoangioblasts and fibroblasts. Mesoangioblasts are derived from a muscle biopsy of the patient, fibroblasts from a skin biopsy—both may be taken together from the abdominal wall at the time of the gastrostomy procedure for the newborn.
4. Culture the seeded scaffold in chamber in defined proliferation medium for 2 days and defined differentiation medium for 9 days maintained at humidified 37° C. with 5% $CO_2$ with external control of the chamber conditions via a bioreactor controller.
5. Deliver epithelial cells onto the luminal side of the oesophageal scaffold (primary cells derived from a biopsy of the patient's existing vestigial oesophagus).
6. Following further culture, transport to the operating theatre in the chamber and remove for transplantation to the patient.

Example 14—Characterisation of Fibroblasts Used in Examples 15 to 18

Mouse fibroblasts (mFB) used in all the co-seeding experiments described below were isolated from wild type mouse hindlimb skeletal muscles (extensor digitorum longus—EDL) and diaphragm through enzymatic digestion and plated for expansion. Cells showed classic elongated morphology and size and were positive for Ki67 when expanded in culture, exhibiting proliferation capacity for several passages (FIG. 23). Fibroblasts were also positive for classic markers such as Vimentin and TCF-4.

Example 15—Analyses of Schematic Cell Distribution in Cell Seeding Experiments on Decellularised Rat Scaffolds Decellularised rat scaffolds seeded with hMAB or hMAB+mFB (ratio 85:15) and cultured in static conditions were fixed, cryosectioned and stained for human Nuclei and DAPI as previously described. Sections were scanned to detect and count all the cells present in the scaffold and create a schematic distribution of the cells (FIG. 24A). From the collection of schematic and polar distribution (cell distribution corrected assuming a perfectly circular section, FIG. 24A,B) we detected a clear improvement in cell engraftment and homogeneity of distribution around tissue section in hMAB+mFB seeded scaffolds compared to hMAB alone. The counting of the total number of cells per area confirmed this trend (n≥3, FIG. 24C).

Example 16—Investigation of Cell Migration in hMAB or hMAB+mFB Seeded Scaffolds

To assess the migration capacity of hMAB seeded with or without mFB in the rat decellularised scaffold, we seeded hMAB transduced with a luciferase ZS Green lentivirus (ZsGreen$^+$Luc$^+$hMABs). Transduction of the cells was confirmed using flow cytometry and a pure population of transduced cells was obtained using FACS sorting. Bioluminescence imaging (BLI) was used to track the cells on the scaffold using an In Vivo Imaging System (IVIS). The cells were non-invasively tracked for migration every 24 h (FIG. 25A). BLI was successfully detected from the seeded cells and images were analysed to quantify the radiance emitted every 24 h (FIG. 25B). To calculate the migration of cells, BLI was determined from 8 different Regions of Interest (ROIs) positioned from the centre of the injection point (FIG. 25C). Radiance measured in the ROIs from 3 to 6 (central ROIs) after 1 day of culture highlighted a higher BLI in scaffolds seeded with hMAB alone (triangles, FIG. 25D). This was perfectly in line with the experimental set up since only hMAB were Luc$^+$ and their initial number was higher in respect to the co-seeding condition (ratio 85:15). Nevertheless, after an expected decrease in cell number in the following days, at 3 and 5 days of culture, the total radiance detected from the hMAB+mFB scaffolds (squares) was comparable or higher than the ones with hMAB alone, showing a clear cell growth and migration in the different ROIs throughout the culture. At day 5, the co-seeded scaffolds showed a higher radiance when compared to hMAB alone, in particular at the ROI 3 and 6 farther from the injection point (between ROI 4 and 5), highlighting the presence of a larger number of cells migrating along the scaffold (FIG. 25D).

Cell migration was determined also using the MTT viability assay, which allowed visualisation of cells on the seeded scaffolds after 6 days of culture (FIG. 26). Tubular scaffolds seeded with $8.5 \times 10^5$ hMAB or $1 \times 10^6$ hMAB with/without mFB (ratio 85:15) were cultured in static condition for 6 days and then incubated with MTT solution for 4 hours. Formazan-positive cells were visible within the scaffold highlighting the differences in the migration pattern and extent among the 3 conditions (FIG. 26A). Images of flat open scaffolds were analysed for cell migration measuring the colour intensity along 8 random lines draw radially from the centre of the cell clusters to the edge of the scaffold using ImageJ software (representative line A-B, FIG. 26A, centre). The Gray value graph obtained from all the lines was used to calculate the distance in pixels covered by the cells, considering the distance between the 2 plateaus (representative graph and measure in FIG. 26B). The average distance covered in mm by the cells in co-seeded scaffolds was higher than the other 2 conditions with hMAB alone (n=3, counting performed by 3 independent operators in blind, FIG. 4C), confirming the same trend determined with BLI quantification with IVIS.

Example 17—Deeper Investigation of Cell Distribution in hMAB+mFB Co-Seeded Scaffolds Cultured in Static and Dynamic Conditions Sections of decellularised rat oesophagi co-seeded with hMAB+mFB and cultured in static or dynamic conditions, were stained and scanned as previously described to detect and count all the cells present in the scaffold. Schematic distribution of the cells (FIG. 27A) and polar distribution (cell distribution corrected assuming a perfectly circular section, FIG. 27B) showed an overall tissue growth and better homogeneity of distribution around tissue section in scaffolds cultured in the bioreactor compared to the static condition. The counting of the total number of cells per area confirmed this significant difference (n≥3, *p<0.05, FIG. 27C). The proportion between hMAB and mFB in scaffolds cultured in dynamic condition was determined from cell counting in random sections stained for DAPI and human Nuclei to assess the eventual overgrowth of fibroblasts. After 11 days of culture, mFb were present only for the 14% on the total number of cells, showing no uncontrolled expansion of these cells within the scaffold (n≥3, FIG. 27D).

Furthermore, using the IVIS to track the cells seeded in the rat scaffold (Luc$^+$hMAB+mFB) and cultured in the glass bioreactor for 7 days, we were able to visualise the cell distribution along the scaffold throughout the culture (FIG. 28A). IVIS images were collected at different time points, showing a clear cell invasion starting from the injection points (green-yellow-read clusters at day 1) towards a more homogenous distribution and tissue coverage at day 7. Radiance values detected from the images collected at the different time points highlighted a decrease in cell number after the first few days of culture, recovered after 7 days (FIG. 28B).

Example 18—Mesoangioblast Proliferation and Differentiation Level in Static and Dynamic Conditions in Presence of Fibroblasts Sections of decellularised rat oesophagi co-seeded with hMAB+mFB and cultured in static or dynamic conditions, were stained for human Nuclei, SM22 (smooth muscle differentiation marker) and DAPI and scanned as previously described to detect and count all the cells present in the scaffold (black area, FIG. 29A). The representative schematic distribution of the cells in FIG. 29A shows the automated discrimination between the differentiated cell types: SM22$^+$hMAB; SM22$^+$mFB; SM22$^+$hMAB; SM22$^+$ mFB, all in greyscale. The maps highlighted the distribution of differentiated cells in scaffolds cultured in the bioreactor compared to the static condition. When the bioreactor was providing mechanical stimulation and better access to the differentiation media, SM22$^+$ cells were present in all the layers of the scaffold and homogenously distributed, while constructs cultured in static condition displayed smooth muscle cells only on the surface of the matrix (FIG. 29A,C). The calculation of the percentage of SM22$^+$ cells after static and dynamic culture counted in random images of different sections (n≥3) confirmed the significant higher percentage of smooth muscle differentiated cells in scaffolds grown in the bioreactor (**p<0.001, FIG. 29B). Interestingly, about 10% of SM22$^+$ cells were fibroblasts and their contribution was comparable in the 2 culture conditions. In dynamic cultured samples co-seeded with hMAB+mFB, mature differentiation towards smooth muscle was further confirmed with the immunostaining for αSMA and calponin (FIG. 30). Cells showed co-expression of SM22 and both αSMA and calponin in all the layers of the scaffold, demonstrating a mature level of differentiation.

The invention claimed is:
1. A method of producing a tissue construct suitable for implantation into a subject, the method comprising the steps of:
 (i) providing an acellular scaffold;
 (ii) seeding a combination of mesoangioblasts and fibroblast cells into or onto the scaffold wherein the ratio of mesoangioblasts:fibroblasts used for seeding is 50:50 to 99:1; and
 (iii) culturing the seeded scaffold to produce said construct.
2. The method as claimed in claim 1 wherein the subject is human.

3. The method as claimed in claim 1 wherein said tissue construct is for implantation in a luminal organ, or to replace said organ.

4. The method as claimed in claim 1 wherein said tissue construct is an oesophageal construct for a neonate or infant.

5. The method as claimed in claim 1 wherein the ratio of mesoangioblasts:fibroblasts used for seeding is 65:35 to 90:10.

6. The method as claimed in claim 5 wherein ratio is about 85:15.

7. The method as claimed in claim 1 wherein the cells are seeded simultaneously or sequentially within or about 1, 2, 3, 4, 5, 6, 7, 8, 9, 10, 11, 12, 24, 36 or 48 hours of each other.

8. The method as claimed in claim 1 wherein the cells are delivered in a liquid or gel medium and the total concentration of cells in the medium is between $1\times10^8$ to $1\times10^{10}$ cells/mL.

9. The method as claimed in claim 1 wherein seeding is by injection into the scaffold.

10. The method as claimed in claim 9 wherein the injection volume is 1 to 50 µL or 5 to 10 µL.

11. The method as claimed in claim 9 wherein the flow rate used for seeding the cells is in the range of 1 to 25 µL/s or 1 to 10 µL/s.

12. The method as claimed in claim 9 wherein the seeding comprises multiple injections to achieve a density of cells of at least $10^5$, $10^6$ or $10^7$ cells/5 mm length.

13. The method as claimed in claim 1 wherein the mesoangioblast and fibroblast cells are autologous to an intended recipient.

14. The method as claimed in claim 1 wherein the mesoangioblast cells express the following markers: AP; NG2; and/or are passaged at least twice prior to seeding.

15. The method as claimed in claim 1 wherein the scaffold is tubular.

16. The method as claimed in claim 1 wherein the scaffold is synthetic.

17. The method as claimed in claim 1 wherein the scaffold is decellularized.

18. The method as claimed in claim 17 wherein the scaffold is derived from a luminal organ.

19. The method as claimed in claim 17 wherein the scaffold is of non-human origin.

20. The method as claimed in claim 19 wherein the scaffold is porcine-derived, preferably a decellularized piglet oesophagus.

21. The method as claimed in claim 17, which comprises the steps of:
(ia) providing a scaffold derived from a biological source;
(ib) decellularizing the scaffold to provide an acellular scaffold.

22. The method as claimed in claim 1 wherein following seeding of the cells onto the scaffold, the cells are allowed to adhere to the scaffold until at least 60% of the cells adhere prior to placing the seeded scaffold in culture medium.

23. The method as claimed in claim 1 wherein after the scaffold is seeded, the construct is cultured under sterile conditions in one or more media suitable for growth and differentiation of the mesoangioblast cells in a bioreactor.

24. The method as claimed in claim 23 wherein the scaffold is cultured under static culture conditions followed by dynamic culture conditions.

25. The method as claimed in claim 23 wherein the scaffold is cultured under dynamic culture conditions for between 3 and 28 days.

26. The method as claimed in claim 24 wherein during dynamic culture the medium is changed from proliferation to differentiation medium.

27. The method as claimed in claim 26 wherein the dynamic culture comprises at least 1 day of proliferation medium and at least 6 days of differentiation medium.

28. The method as claimed in claim 23 wherein the culture conditions subject the construct to pulsatile or peristaltic forces.

29. The method as claimed in claim 23 wherein the bioreactor incorporates a removable cassette which can be transferred from a decellularization bioreactor, subjected to seeding, and then introduced to a recellularization bioreactor.

30. The method as claimed in claim 1 wherein following step (iii) said tissue construct is implanted into an ectopic site in a subject for vascularization.

31. The method as claimed in claim 1 comprising a further step of epithelising said tissue construct on at least one surface.

32. The method as claimed in claim 31 wherein the construct has a luminal shape, and is epithelised on the inner luminal surface.

33. The method as claimed in claim 3 wherein the luminal organ is the oesophagus or bowel.

34. The method as claimed in claim 5 wherein the ratio of mesoangioblasts:fibroblasts used for seeding is 70:30 to 90:10.

35. The method as claimed in claim 5 wherein the ratio of mesoangioblasts:fibroblasts used for seeding is 80:20 to 90:10.

36. The method as claimed in claim 5 wherein the ratio of mesoangioblasts:fibroblasts used for seeding is 83:17 to 87:13.

* * * * *

UNITED STATES PATENT AND TRADEMARK OFFICE
CERTIFICATE OF CORRECTION

PATENT NO. : 10,632,229 B2
APPLICATION NO. : 15/757729
DATED : April 28, 2020
INVENTOR(S) : Paolo Decoppi, Luca Urbani and Anna Urciuolo Page 1 of 1

It is certified that error appears in the above-identified patent and that said Letters Patent is hereby corrected as shown below:

In the Claims

At Column 24, Claim 1, Line 56, "suitable" should be deleted.

Signed and Sealed this
Sixteenth Day of June, 2020

Andrei Iancu
*Director of the United States Patent and Trademark Office*